United States Patent [19]

Shaw et al.

[11] Patent Number: 5,089,418
[45] Date of Patent: Feb. 18, 1992

[54] ANALYZER FEATURING A CIRCULAR TRACK OF CARTRIDGES CENTERED ON AN INCUBATOR AND METHOD OF USE

[75] Inventors: James D. Shaw, Hilton; Martin F. Muszak; Nicholas Want, both of Rochester, all of N.Y.

[73] Assignee: Eastman Kodak Company, Rochester, N.Y.

[21] Appl. No.: 556,693

[22] Filed: Jul. 20, 1990

Related U.S. Application Data

[63] Continuation-in-part of Ser. No. 500,651, Mar. 28, 1990, abandoned.

[51] Int. Cl.$^5$ ..................... G01N 21/00; G01N 35/00
[52] U.S. Cl. ......................... 436/46; 422/63; 422/64; 436/47; 436/48
[58] Field of Search ............... 422/63, 64, 65; 436/43, 436/45, 46, 47, 48

[56] References Cited

U.S. PATENT DOCUMENTS

| | | | |
|---|---|---|---|
| 3,728,227 | 4/1973 | Elson et al. | 195/127 |
| 4,152,390 | 5/1979 | Nosco et al. | 422/65 |
| 4,224,032 | 9/1980 | Glover et al. | 436/46 |
| 4,296,069 | 10/1981 | Smith et al. | 422/64 |
| 4,296,070 | 10/1981 | Montalto et al. | 422/65 |
| 4,424,191 | 1/1984 | Jakubowicz | 422/65 |
| 4,512,952 | 4/1985 | Blanding et al. | 422/64 |

OTHER PUBLICATIONS

Eastman Kodak User Manual Publication No. XP3080-13, pp. 5, 6 & 12 (1986).

Primary Examiner—Robert J. Warden
Assistant Examiner—Theresa A. Trembley
Attorney, Agent, or Firm—Dana M. Schmidt

[57] ABSTRACT

There is disclosed an apparatus useful in an analyzer, comprising a first mechanism for moving a stack of elements around at least one generally circular, horizontal track, a second mechanism for temporarily holding a stack on the track, and a third mechanism for altering the second mechanism between two states, one which holds the stack on the track and the other which releases the stack from the track.

37 Claims, 17 Drawing Sheets

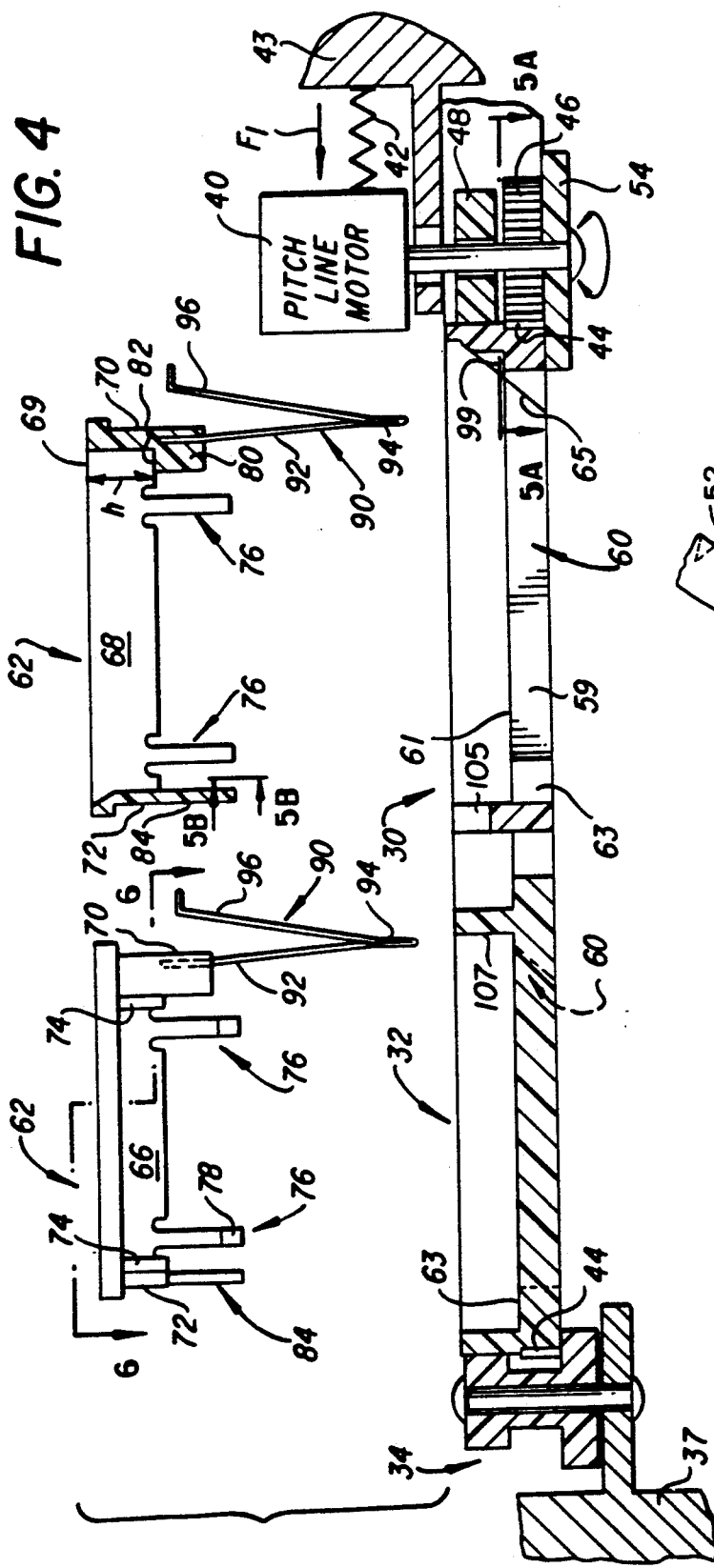
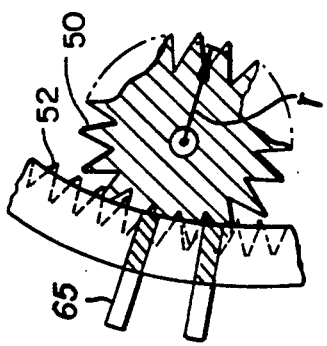
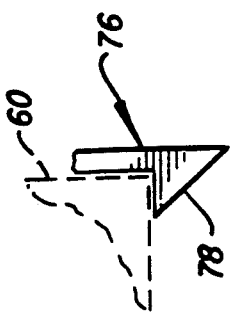
FIG. 4
FIG. 5A
FIG. 5B

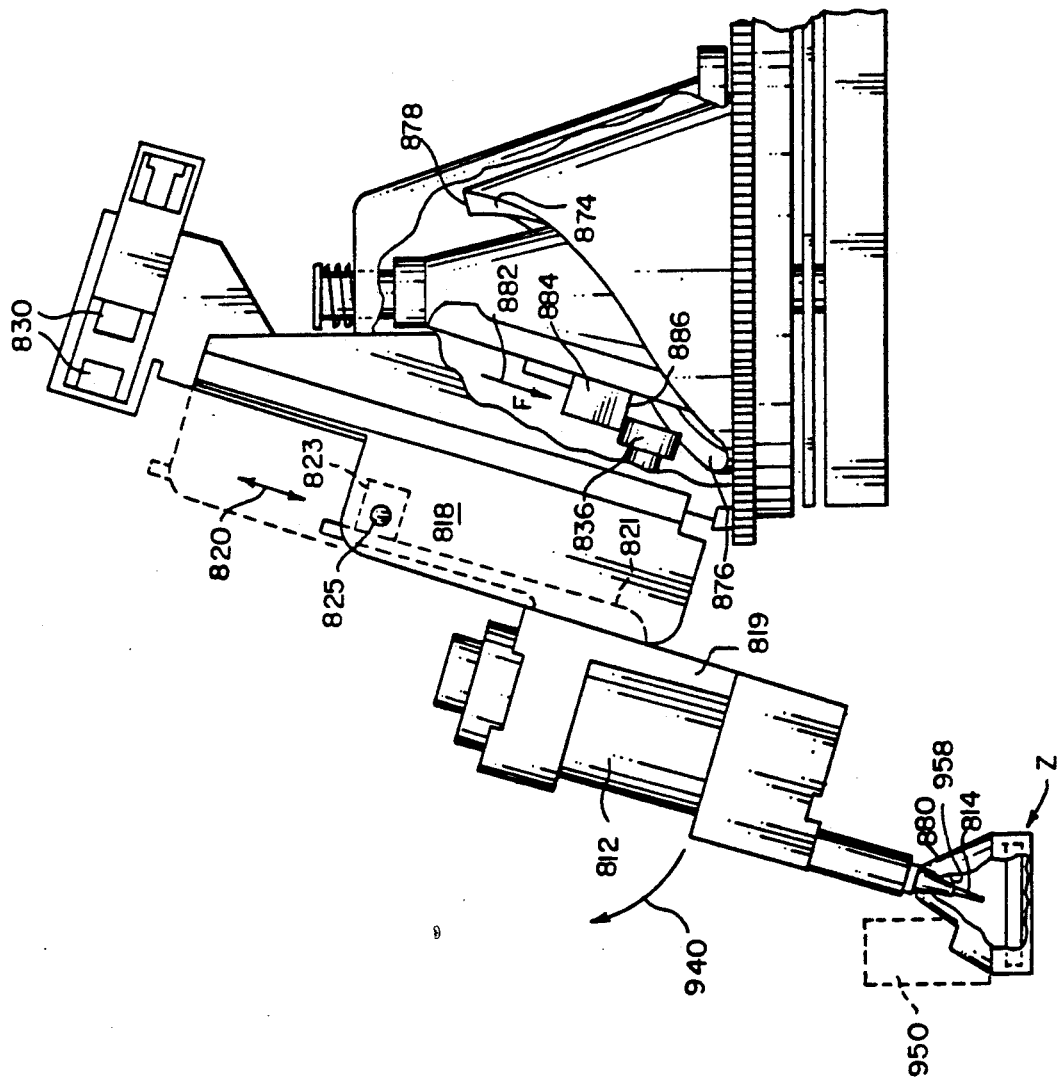

ANALYZER FEATURING A CIRCULAR TRACK OF CARTRIDGES CENTERED ON AN INCUBATOR AND METHOD OF USE

RELATED APPLICATIONS

This is a continuation-in-part application of U.S. Ser. No. 500,651 filed on Mar. 28, 1990, abandoned.

OTHER RELATED APPLICATIONS

Commonly-owned U.S. Ser. No. 349,451 filed by us on May 9, 1989 entitled "Flexible Pusher Blade and Housing", describes a pusher blade for loading test elements from test-element cartridges mounted to move along parallel paths. The invention therein is not claimed, however, as occupying concentric rings around a central incubator.

Commonly-owned U.S. Ser. Nos. 293,712 and 293,718 filed on Jan. 5, 1989 and entitled "Reciprocating Transfer Mechanism and "Incubator and Analyzer with Improved Cap Raising Means", respectively, provide for an incubator that will incubate both CM type and PM type test elements. However, there is no disclosure of cartridges or their mounting means of any type to supply test elements to the incubator.

Commonly-owned U.S. Ser. No. 556,692 entitled "Dispensing Mechanism" is being cofiled herewith by Shaw et al. This describes and claims the pump mechanism per se, that is shown herein as FIGS. 18-23B.

FIELD OF THE INVENTION

This invention relates to an analyzer and a method for the economical assaying of components of a body liquid, particularly designed for high volume throughput occupying a minimum amount of space.

BACKGROUND OF THE INVENTION

Large liquid analyzers such as the blood analyzers described in U.S. Pat. No. 4,512,952 have been very successful in testing body liquids using dried test elements sometimes identified as "slides". One of the reasons for this has been the high throughput that such analyzers provide, and the high degree of accuracy and precision that is possible. On the other hand, there remain some minor disadvantages. These stem from the fact that there have been used in such analyzers, three different kinds of slide test elements—colorimetric endpoint types, hereinafter "CM" types; rate types; and potentiometric types, hereinafter "PM" types. Each type has needed its own incubation and reading station. Examples are shown in, e.g., the aforesaid U.S. Patent. Due to the need for three incubators and their separate read stations, such analyzers have taken up considerable space. Furthermore, triplicating the incubators and read stations has added considerably to the cost.

A further disadvantage of some analyzers has been the amount of space required. Every time an additional function is added, the apparatus for that function has been simply "added on", producing a machine wherein no attempt is made to use space most efficiently.

Japanese Kokai 61/209341 describes a rotating incubator, FIG. 5, which is said to be useful, p. 14, for CM type test elements or rate-type. However, PM types are not mentioned, nor are the test elements supplied from sources that provide for maximum utilization of space in the analyzer.

Therefore, prior to this invention, there has been the need for a blood analyzer having high throughput, accuracy and precision as in the above-noted prior analyzer, but using fewer stations in a more efficient manner to require less room and less cost.

SUMMARY OF THE INVENTION

We have constructed an analyzer that allows all three of the above-mentioned types of dried test elements to be assayed on one incubator, and which solves the above-noted problems.

More specifically, in accord with one aspect of the invention, there is provided an analyzer for assaying for analytes of a body liquid on dried test elements, the analyzer including means for temporarily storing a plurality of stacks of dried test elements, the test elements in any one stack being for the same assay while each stack is generally for a different assay selected from any one of potentiometric, colorimetric or rate-type test elements, an incubator for test elements taken from a stack, and means for detecting a change in a test element after incubation in the incubator. The analyzer is improved in that it further includes means defining at least one generally circular, horizontal path generally centered on the incubator, first moving means for moving the stack-storing means around the at-least-one path, means for temporarily holding a stack on the moving means, the holding means comprising being capable of at least two alternate states, one which holds a cartridge on the path and the other which releases a cartridge from the path, means for alternating the holding means between the two states, and means for transferring a test element to the incubator from any stack held on the path, whereby the incubator can be used to incubate all three types of test elements.

In accord with another aspect of the invention, that analyzer is improved in that the above-noted holding means comprises a member mounted on a track to move between a first position that holds a cartridge for the stack and a second position that releases a cartridge, second moving means being provided for moving the holding member between the two positions.

In accord with yet another aspect of the invention, there is provided apparatus for temporarily storing a stack of planar, slide-like elements in a predetermined vertical position. The apparatus comprises means defining at least one generally circular, horizontal path and first moving means for moving a stack of elements around the at-least-one path, means for temporarily holding a stack on the first moving means, said holding means comprising a member mounted on the moving means to move between a first position that holds a cartridge for the stack and a second position that releases a cartridge, and second moving means for moving the holding member between the positions.

In accord with still another aspect of the invention, there is provided apparatus for temporarily supporting a stack of planar, slide-like elements, in a cartridge held in a predetermined vertical direction. The apparatus comprises means for temporarily holding a cartridge of elements, means for moving said holding means along a generally circular path around a center, and means for slidably moving said holding means between two positions on a radius of said circular path, one of said positions being one which allows a cartridge to fall, and the other of said positions being one which holds up a cartridge.

A further aspect of the invention comprises a method for supplying a test element from any one of three different kinds to an incubator. This method comprises the steps of supplying slide-like test elements selected from CM-type, rate-type, and PM-type elements, as a plurality of stacks wherein the test elements of each stack are identical within the stack, mounting the stacks on at least one generally circular path surrounding a central incubator, moving the stacks around the path until a selected stack reaches a predetermined position, and transferring a test element from the stack at the predetermined position to the incubator.

Accordingly, it is an advantageous feature of the invention that an analyzer for all three types of test elements is provided that minimizes the space needed, without sacrificing through-put.

It is a related advantageous feature that such an analyzer is laid-out in a highly efficient configuration that requires less space.

It is another advantageous feature of the invention that apparatus and a method are provided for efficiently and easily loading any one of three different kinds of test elements into a single incubator.

Other objects and advantages will become apparent upon reference to the following description of the preferred embodiments, when read in light of the attached drawings.

BRIEF DESCRIPTION OF THE DRAWINGS

FIG. 4 is a fragmentary exploded section view taken generally along the line IV—IV of FIG. 3, with the nesting frames added;

FIG. 5A is fragmentary section view taken generally along the line VA—VA of FIG. 4;

FIG. 5B is a fragmentary section view taken generally along the line VB—VB of FIG. 4;

FIG. 21 is a partially broken away, elevational view illustrating the cam follower in its lowermost position, wherein it is biased by the down-loading cam;

DESCRIPTION OF THE PREFERRED EMBODIMENTS

The invention is hereinafter described in detail with respect to preferred embodiments featuring certain kinds of dried test elements, and preferred specific mechanisms a) for supplying and dispensing body liquid for assaying, b) for unloading test elements from cartridges, and c) for incubating such test elements after body liquids are dispensed thereon. In addition, the invention is useful regardless of the chemistries used in the dried test elements, and the type of cartridge, and regardless of the body liquid assayed or the specific mechanisms contributing the noted functions of supplying and dispensing body liquid, and unloading and incubating test elements.

Orientations such as "up", "horizontal", "level" and the like are used herein with respect to the orientations preferred during normal usage.

The preferred test elements for use in this invention are the dried test elements identified in patents such as U.S. Pat. Nos. 4,336,091 (PM-type), and 3,992,158 and 4,258,001 (for both CM-type and rate type). Useful elements also include all three noted types as they are available under the trademark "Ektachem" slides from Eastman Kodak Company.

The test elements are provided as stacks within the storage means described below, each stack preferably comprising identical test elements for a single assay. Any method of providing such stacks is useful. Preferably, each stack is housed in a cartridge, the term hereinafter used. Most preferably, such cartridges are constructed as described in any of U.S. Pat. No. Re. 30,595; U.S. Pat. Nos. 4,187,077; 4,151,931; and 4,190,420. Additionally, the cartridges available under the trademark "Ektachem" slide cartridges for specific assays, from Eastman Kodak Company, can be used.

Figure 1:
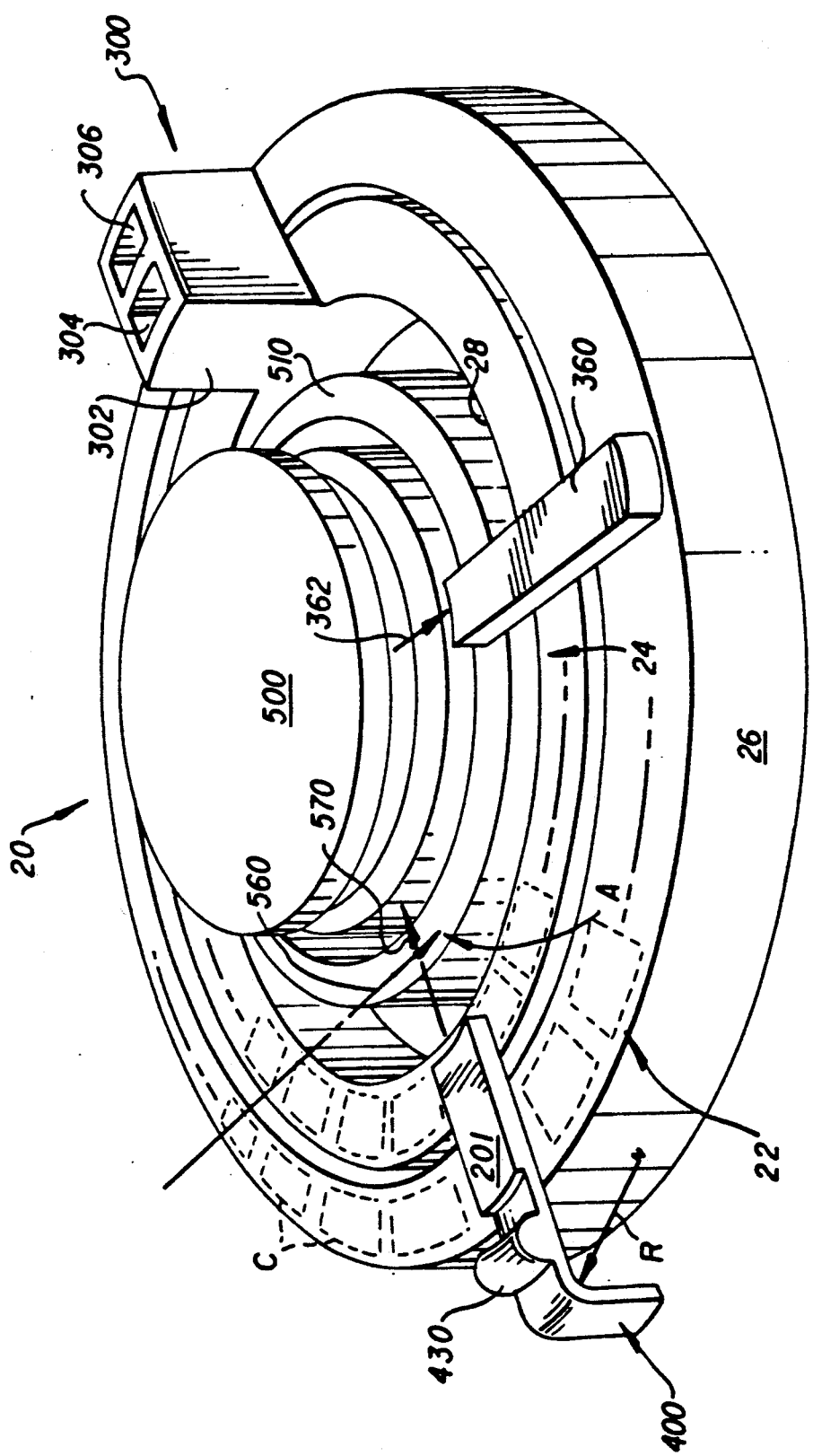
FIG. 1 is a perspective view of an analyzer constructed generally in accordance with the invention, the dispensing mechanism of FIG. 18 having been omitted for clarity.
Figure 2:
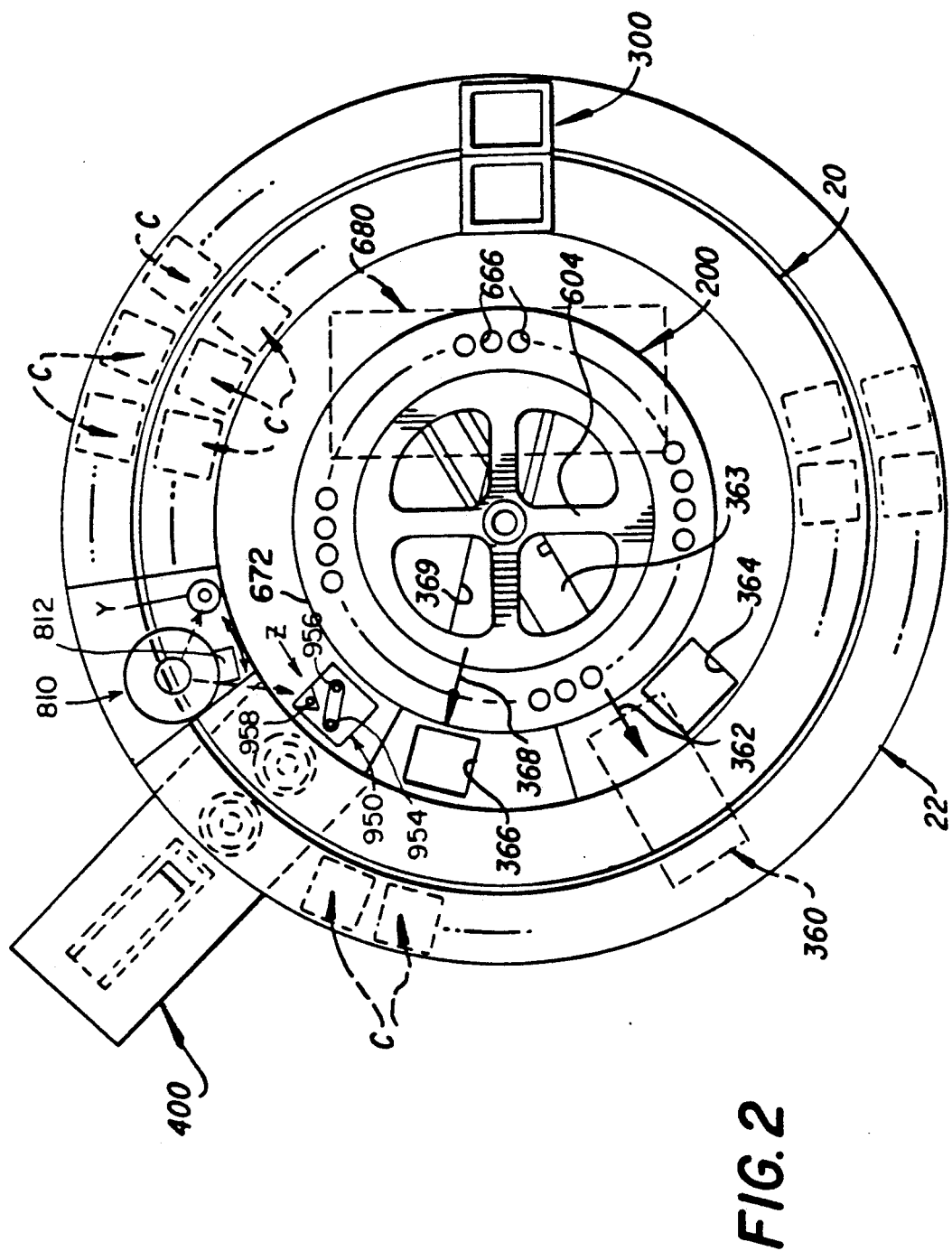
FIG. 2 is a partially schematic, plan view depicting the general arrangement of the parts of the analyzer.

In accordance with the invention, analyzer 20 comprises, FIGS. 1 and 2, means for temporarily storing a plurality of stacks of test-elements are provided in the form of cartridges C. Means are further provided to define at least one, and preferably two, concentrically disposed paths 22 and 24, preferably centered on point c, FIG. 3, the center of the incubator and of the analyzer. That is, each path 22 or 24 extends around a single incubator 500 that is disposed so as to be generally centered within the paths, thus optimizing the use of space in the analyzer. A cartridge-loading station 300, FIGS. 1 and 2, is disposed above the paths to one side of incubator 500. An electrometer 360 is disposed above the paths at another side of incubator 500, and a test-element transfer device 400 is provided above the paths at yet another side of incubator 500 to load a test element into incubator 500 from any cartridge on the paths. A reference liquid dispensing mechanism 810 is also provided, FIGS. 2 and 8B, above the paths to dispense the reference liquid to ISE (ion-selective electrode) test elements as needed. A stationary support surface 510 is provided as an annular ring between path 24 and incubator 500, to cooperate with the liquid dispensers, described hereinafter. The analyzer controls, not shown, comprise one or more microprocessors connected to suitable input and output devices, as is conventional.

Figure 8A:
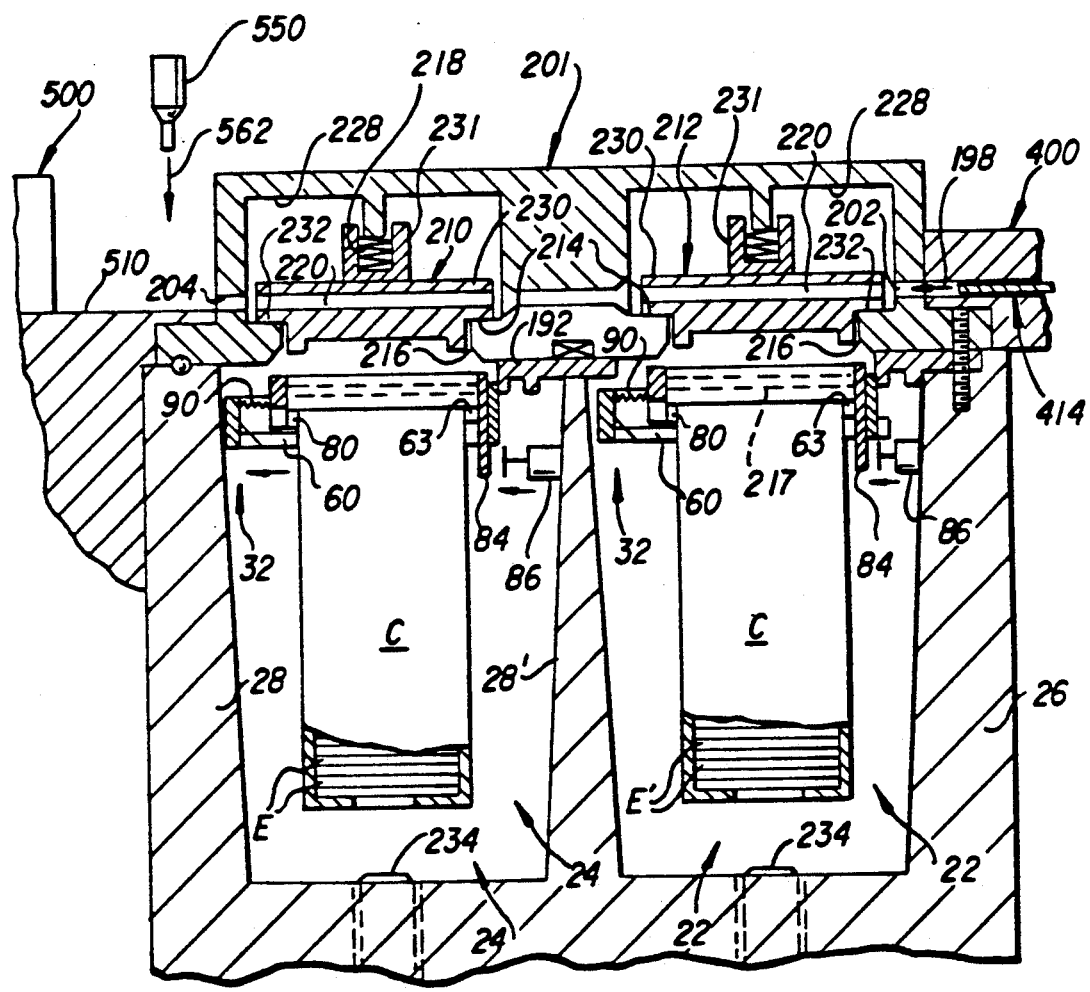
FIG. 8A is a fragmentary elevational view in section, taken from behind transfer device 400 as seen in FIG. 1, illustrating the cartridge-mounting means assembled in place to cooperate with a pusher blade of device 400 to dispense test elements to the incubator.

Referring more specifically to paths 22 and 24, each of these is separately housed within a frame comprising fixed exterior walls 26 and 28, respectively, FIGS. 1 and 8A. Most preferably, walls 26 and 28 can be combined to provide a single common wall 28' between the paths, FIGS. 8A and 8B.

To move cartridges around each path, within each housing for each path, an annular ring 30 or 32 is rotatably mounted, FIGS. 3-5 and 8A. Follower rollers 34 or 36, respectively, are strategically placed on frame portion 37 of the analyzer, FIG. 4, to partially constrain the rings on the horizontal and vertical directions. The final constraint is a drive motor 38 or 40, respectively, FIGS. 3 and 4. Each drive motor is biased by a conventional spring 42, FIG. 4, mounted on a frame member 43 of the analyzer to exert a radial force $F_2$ or $F_1$ against the ring, FIGS. 3 and 4. The drive connection is via a ring gear 44 mounted on the outside of ring 30 and the inside of ring 32, and a pinion gear 46 on the drive motor. Motors 38 and 40 are preferably conventional pitch-line motors-that is, in addition to the pinion gear, there is a smooth roller 48 mounted integrally with and above the pinion gear, and the radius "r", FIG. 5A, of this roller is adjusted to insure that teeth 50 of the pinion gear always engage teeth 52 of the ring gear on the pitch line. Additionally, each motor 38, 40 preferably includes a rotating disk 54 that provides underlying vertical support of the ring, FIGS. 3 and 4.

Each of the rings 30 and 32 has cut-out portions 60 shaped and sized to accommodate a test-element cartridge, FIG. 8A. In ring 30, thirty-five such cut-outs are preferably placed, with a fewer number in ring 32, FIG. 3.

In accordance with another aspect of the invention, holding means are included with each of paths 22 and 24, and with each ring 30 and 32, to temporarily hold a cartridge on the ring, preferably in a vertical orientation. The holding means are constructed to operate between at least two alternate states; one of which holds the cartridges as noted, and the other of which releases the cartridge from the ring, preferably to fall away from the ring.

Any such holding means can be used. Highly preferred is one which cooperates with the upper portion of each ring and which moves with respect thereto to release a cartridge. More specifically, an upper, horizontal support surface 61 is provided on each ring around each cut-out portion, FIG. 4. Sidewall 59 of each cut-out 60 is generally oriented radially with respect to the center of ring 30 or 32, FIG. 3. As seen in detail in plan, FIG. 6, each cut-out portion includes at the outer end, a pair of shoulders 63 projecting out into the overall area normally occupied by a cartridge's upper end, FIG. 8. At the inner end of the cut-out, two diagonally shaped guide flanges 65 are provided, FIGS. 4 and 6. Shoulders 63 thus act as means for holding vertically a cartridge, when such shoulders are correctly spaced with respect to a nesting frame member discussed hereinafter.

Most preferably, the cartridges are temporarily held in each ring by "hanging" them in the cut-out portions, FIG. 8A. A preferred form of such holding or "hanging" means comprises nesting frame members 62 for each cut-out portion, FIGS. 4 and 6-8, that cooperate with shoulders 63. More specifically, each such nesting member 62 comprises a generally rectangular frame having two generally vertical side walls 66, 68 and two generally vertical end walls 70, 72, FIG. 4. Each side wall has preferably two projections 74, FIGS. 4 and 6-7, that serve to ride on the upper supporting surface 61 of the ring, FIG. 7, to keep frame member 62 from falling through cut-out portions 60. In addition, each side wall preferably includes two spring fingers 76 that have a latch shoulder 78, FIG. 5B. The fingers are biased outwardly to releasably hold frame member 62 within cut-out portions 60.

Figure 6:
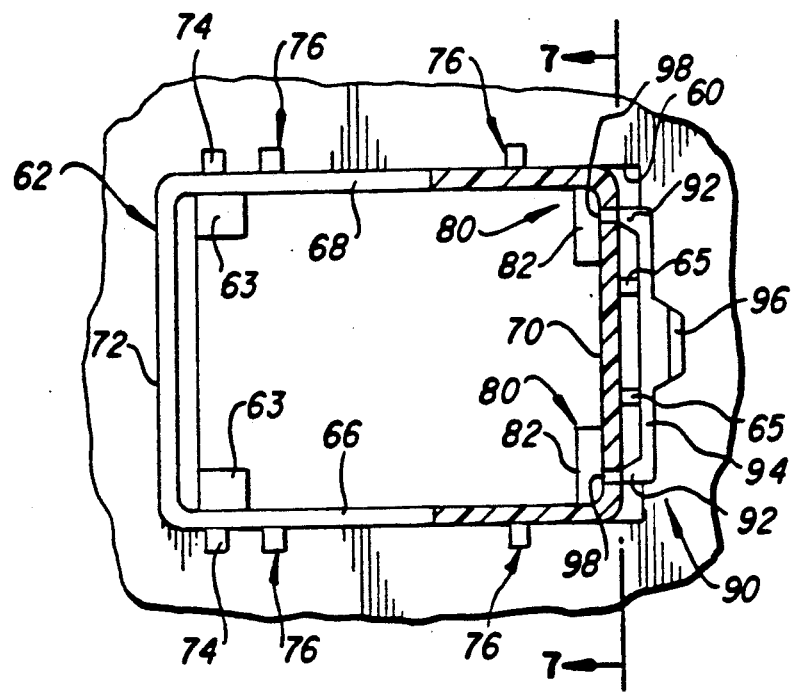
FIG. 6 is a section view taken generally along the line VI—VI of FIG. 5.

To provide part of the means vertically supporting a cartridge, end wall 70 includes at least one and preferably a pair of cartridge support shoulders 80 with a supporting surface 82, FIG. 6. Surface 82 is positioned below top surface 64 of frame member 62 a distance "h", FIG. 4, that equals the distance from top surface 64 to support surface 61 of rings 30 and 32. Shoulder 80 and surface 82 thus project into cut-out portion 60 at generally the same horizontal level as surface 61. When the opposite end wall 72 is pushed over the exposed shoulder 63 of surface 61, surface 82 of nest frame 62 is thus aligned and coacts with surface 61 of shoulder 63 to hold up a cartridge, FIG. 8A.

Figure 7:
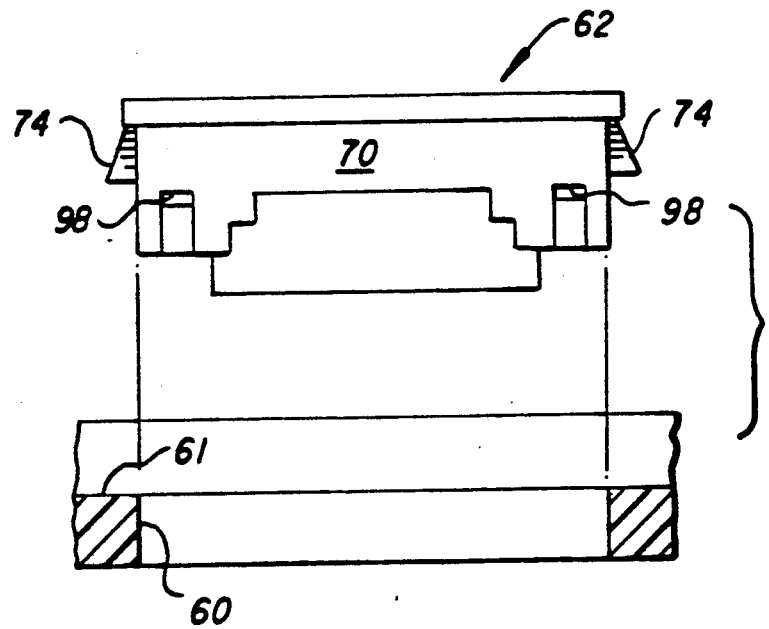
FIG. 7 is an exploded section view taken generally along the line VII—VII of FIG. 6, but without the spring (for clarity)

Opposite end wall 72 includes a downwardly-depending pusher lip 84, FIGS. 4 and 7-8, that cooperates with override means 86 mounted on common wall 28' and wall 26 of the paths, FIG. 8A. The means 86 can be a solenoid, as shown, or a motor-actuated lever, or any automatic conventional actuator. Most preferred is a push member 87 activated by a solenoid 88 to move against the bias of a light spring 89 biased to return member 87 in the direction of arrow 101', FIG. 9. Spring 89 can be a tension spring as shown or a torsion hair spring.

To bias the nesting frame into the "normal" or "hanging" position shown in FIG. 8A, spring means are mounted from end wall 70, FIG. 4. Most preferably, the spring means comprise a compression leaf spring 90 having two interior legs 92, FIG. 6, connected to a body portion 94, from which protrudes upwardly a middle leg 96, FIG. 4. The ends of legs 92 engage apertures 98 of end wall 70, FIGS. 6 and 7, whereas the end of leg 96 rests on surface 61 at position 99 between the two guide flanges 65, FIG. 4.

Alternatively, spring 90 can be an integral part of frame 62.

In use, FIG. 8A, spring 90 (shown schematically in this Figure) "normally" biases nesting frame 62 towards the outside of the ring, generally along a radius of the ring, so that one edge of cartridge C is supported or "hung" by shoulder surface 63 of the ring, and the other is supported by shoulder 80 of nesting frame 62. The exception occurs when override means 86 is actuated in either path 22 or 24. When that occurs, arrow 101 of FIG. 9, nesting frame 62 is moved leftward to compress spring 90. The upper lip of cartridge C is pushed off surface 61 at lip 63 by leftward-moving lip 84 of nesting frame 62. As the frame 62 continues to move leftward, the opening between oppositely-paired shoulders 80 and 63 gradually increases until the spacing "W" is sufficient to allow cartridge C to fall through, arrow 103. Complete exiting of this cartridge from the ring requires, however, the actuation of an exit door 326, discussed hereinafter.

Alternatively, (not shown), cut-outs 60 and frame members 62 could be rotated 90° so as to slide relative to each other (to hold or release a cartridge) along an arc, that is, along a portion of the path traversed by the ring carrying the frame.

Figure 3:
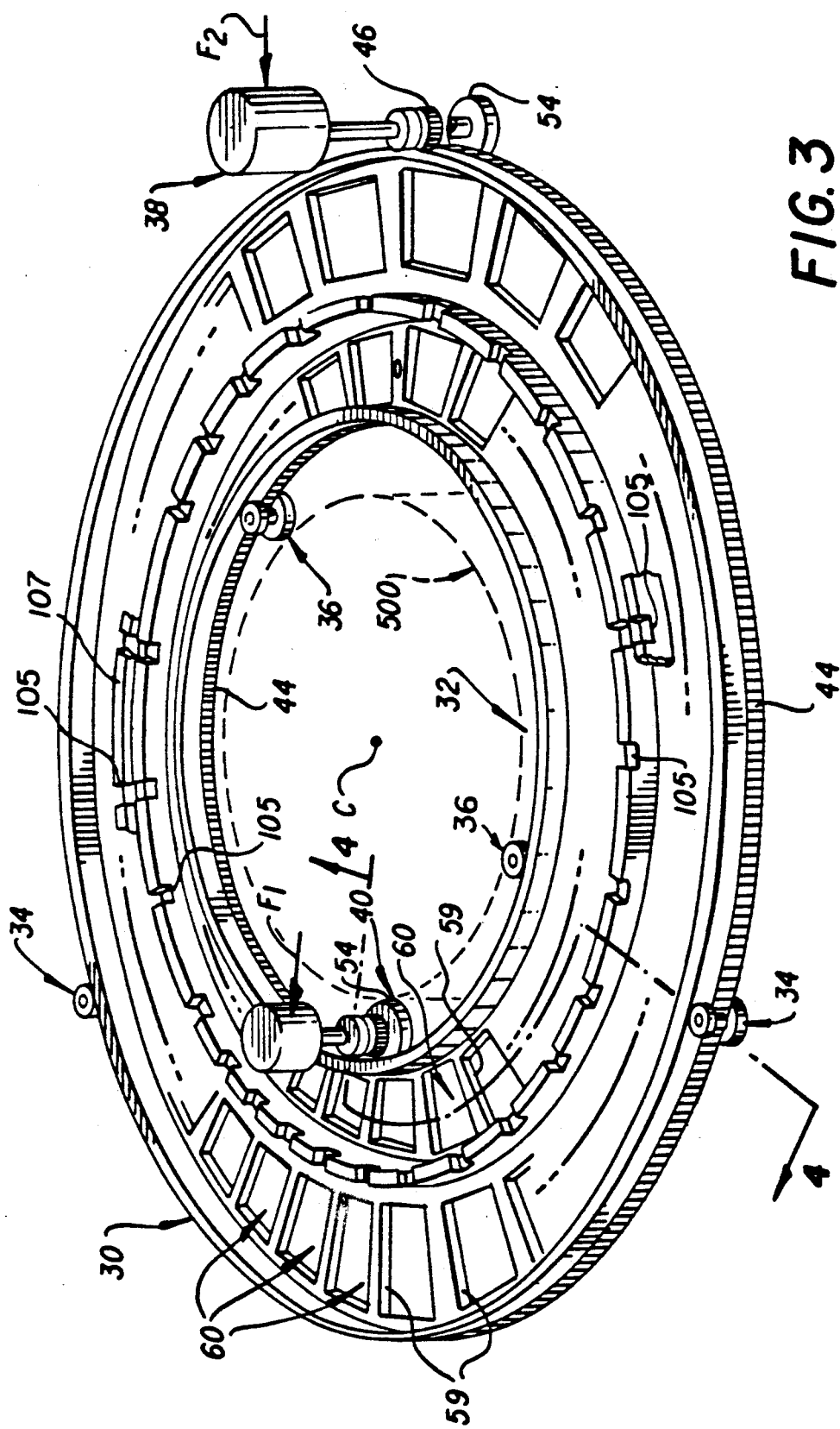
FIG. 3 is a perspective view of a portion of the cartridge-mounting means of the invention, the nesting frames having been removed for clarity.

Notches 105 are preferably included on the outside flange edge of ring 32, and the inside flange edge of ring 30, FIG. 3, to allow a sensor (not shown) to sense that a particular cartridge is in fact at a particular location, e.g., the cartridge load/unload station 300. Each of the cut-out portions 60 can be tracked by the analyzer by flagging one of them as a home position, as is conventional, and then counting the number of offsets from "home".

Figure 10:
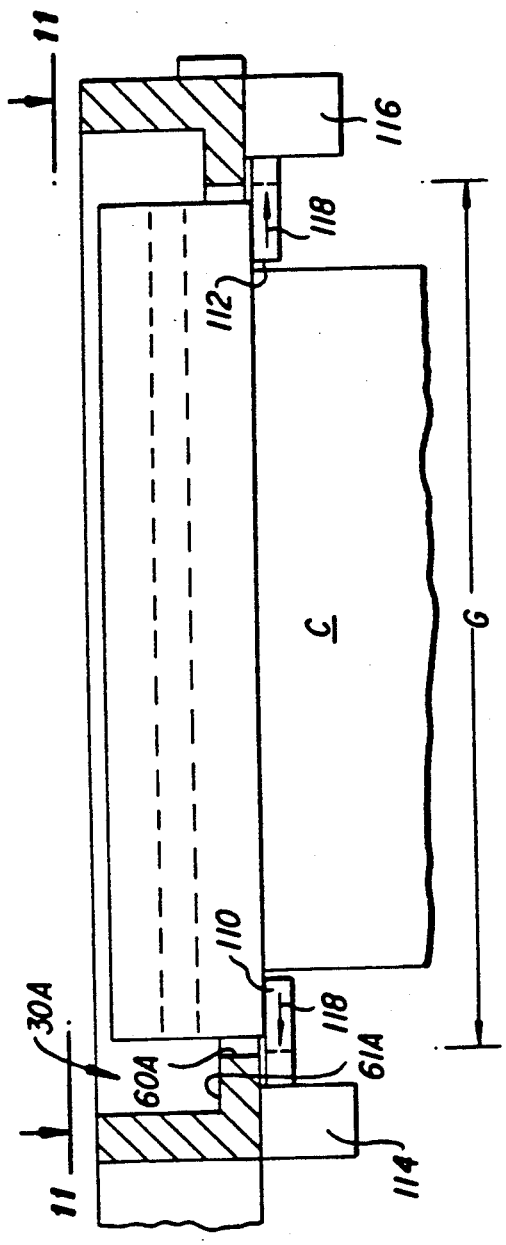
FIG. 10 is a fragmentary elevational view similar to a portion of FIG. 8A, but illustrating an alternate embodiment.
Figure 11:
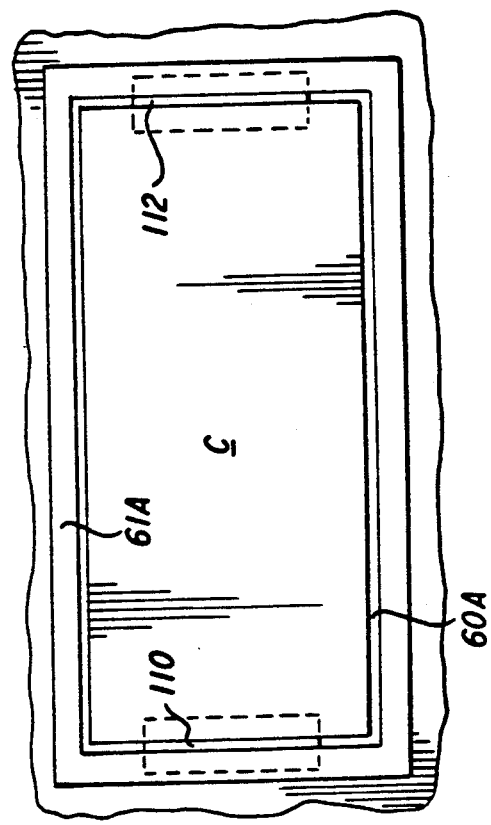
FIG. 11 is a fragmentary plan view taken generally along the line XI—XI of FIG. 10.

Still further, the holding member for the cartridges need not be a full frame that sits and moves within cut-outs in the ring. Instead, as shown in FIGS. 10 and 11, it can be simply solenoid-actuated fingers that hold up the cartridge. Parts similar to those previously described bear the same reference numeral, to which the distinguishing suffix A is appended.

Thus, each ring such as ring 30A can have cut-out portions 60A, that are larger in their interior dimensions, FIG. 11, than the outside dimensions of the upper end of cartridge C. As a result, none of surface 61A surrounding the cut-out portions 60A is used to support the cartridge. Indeed, except for the fingers hereinafter described, cartridge C would fall right through the opening of portion 60A. In this embodiment, the cartridge-holding means comprise oppositely disposed fingers 110, 112, actuated by solenoids 114, 116. When in the solid position shown in FIG. 10, the fingers are extended and hold up a cartridge. When withdrawn to the dotted position, arrow 118, they are separated too far apart to hold a cartridge, so that gap G causes the cartridge to fall through. Alternatively, not shown, one of fingers 110 and 112 can be fixed in the extended position and the other withdrawable a sufficient distance as to create said gap G.

Such solenoid-activatable fingers require a brush-less connection between the rotating ring and a power source. Alternatively, the fingers 110 and 112 can be pivoted so as to be cammable between two positions by a solenoid mounted on the stationary frame. Parts similar to those previously described bear the same reference numeral, to which the distinguishing suffix B is appended.

Figure 12:
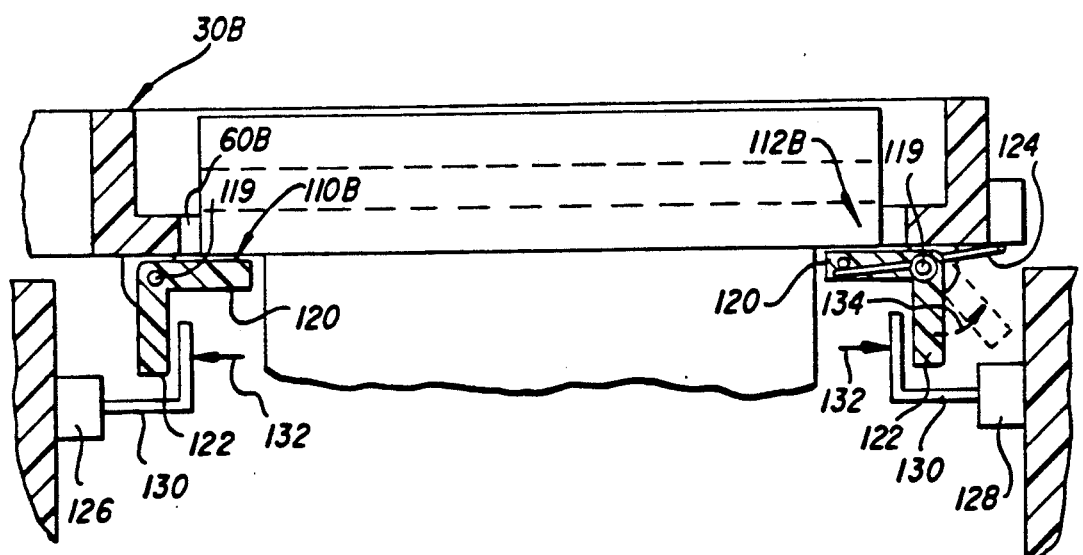
FIG. 12 is a fragmentary elevational view similar to that of FIG. 10, but of yet another alternate embodiment.

Thus, ring 30B has a cut-out portion 60B, FIG. 12, through which a cartridge C will fall, as in FIG. 10, except for opposed fingers 110B and 112B that are pivotably mounted at 119 to move between two alternate states. In one state, as shown in solid lines, they project into the path of the cartridge to catch and hold the cartridge. The fingers are right-angled, with one end 120 locatable under the cartridge and opposite end 122 positioned 90° around and below pivot 119. Spring biasing means such as a compression spring 124, or a torsion spring, preferentially hold fingers 110B and 112B as shown. However, when ring 30B is positioned at the cartridge unload station 300, FIG. 1, the fingers pass by solenoids 126, 128 mounted on the stationary frame, FIG. 12. Such solenoids include arms 130 that are in position to pass outwardly beyond ends 122, without disturbing them, but also to press outwardly against ends 122, arrows 132, forcing the fingers to pivot, arrows 134, to the phantom positions. This in turn causes the fingers to release the cartridges C, which then fall out of position in the ring. A trap door in station 300, described hereafter, allows the falling cartridge to be completely released from its track housing.

Alternatively (not shown), paths 22 and 24 can be defined by circular tracks on which a train of members 62 is caused to ride. An electric motor suitably connected to the analyzer controls can drive such a train on such a track.

Figure 13:
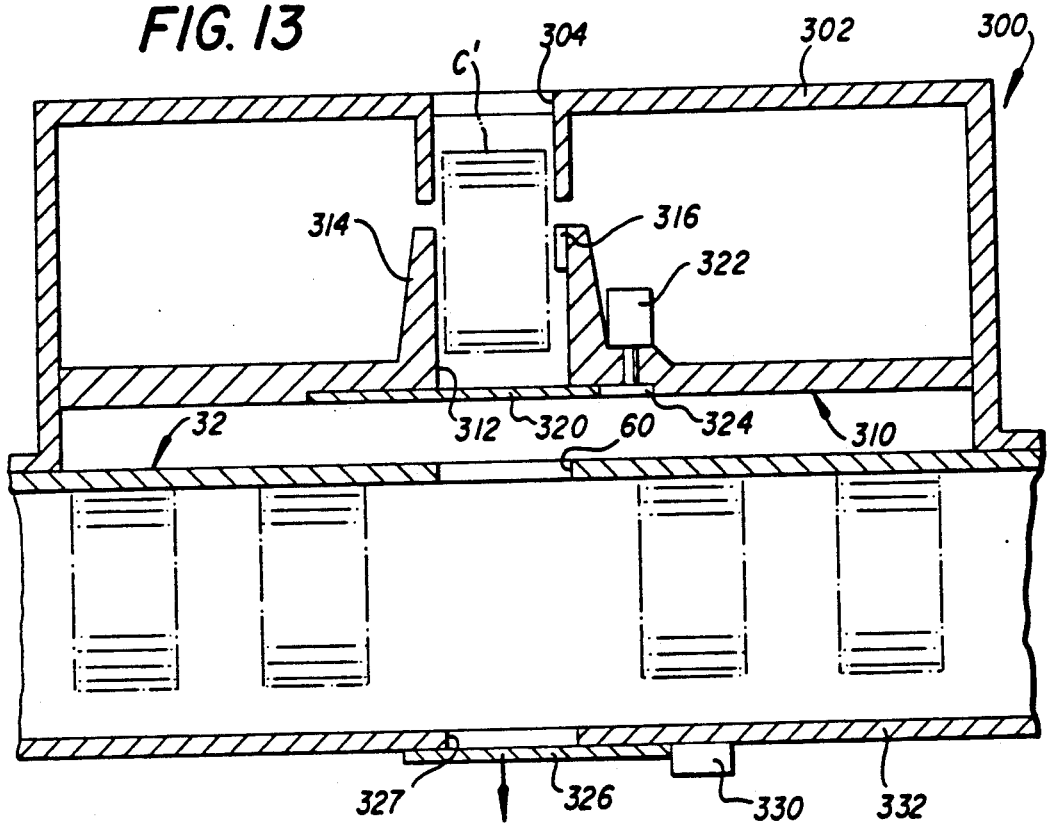
FIG. 13 is a fragmentary elevational view in section of a mechanism for loading cartridges into the mounting means shown in FIG. 8A.

To load and unload cartridge with respect to each of paths 22 and 24, load and unload station 300 is provided. FIGS. 1 and 13. Station 300 comprises a housing 302 that sits on the housing of the two paths, FIG. 13. An opening 304 and 306 is formed in the top surface of housing 302, FIG. 1, each positioned to be aligned with an aperture of the ring below it, when the ring is appropriately centered. Positioned below openings 304 and 306, FIG. 13, is a horizontal wall 310 with an aperture 312 that can be made to be in alignment with cut-out portion 60 of the ring, and that is aligned with opening 304 or 306. An annular shoulder 314 rises from aperture 312, on which a bar code reader 316 is mounted. The bar code reader can be conventional, and is positioned to scan a bar code on an incoming cartridge, as shown.

Aperture 312 is normally closed by a door 320 operated automatically by a motor 322 and any suitable linkage 324 between door 320 and its motor. When an empty portion 60 in ring 32 is positioned in place as shown, with a cartridge C' in position on door 320, motor 322 is actuated to open the door. Cartridge C' falls into place into ring 32, as supported by the structure described for FIGS. 6–12. Ring 32 can then be advanced to move a cartridge into place at the transfer device 400. Spent cartridges, on the other hand, are removed by using door 326, described hereinafter.

Figure 14:
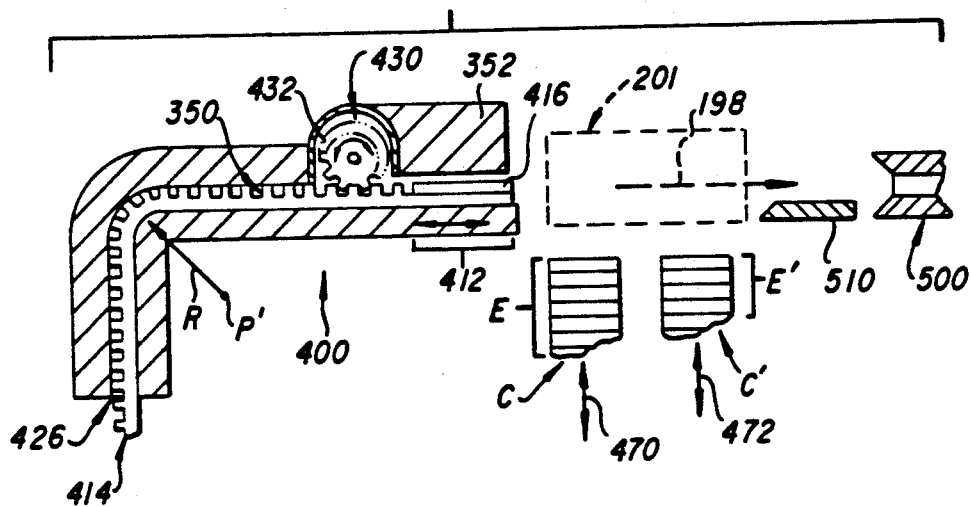
FIG. 14 is a fragmentary elevational view in section of a pusher blade, housing and drive means useful with this invention.

To transfer a test element from a stack of elements E or E' in a cartridge C, device 400 is used, FIGS. 1, 8A and 14. Referring especially to FIG. 14, such a device features a housing 352, and movable within a slot 350 in housing, a pusher blade 414. Any kind of pusher blade is useful, but the following is preferred: All of blade 414 is flexible, except for the front end 412, which is rendered rigid by one or more ribs 416 that extend along the length of the blade. The flexible portion of the blade features notches or a rack 426 that mate with a pinion gear 432 driven in portion 430 of housing 352. As a result, the flexible portion of blade 414 can bend through the curve of slot 350, caused by housing 352 to have a radius of curvature R. This in turn minimizes the lateral space occupied by device 400, FIG. 1.

Blade 414 follows path 198 above the stacks of elements E or E' presented by cartridges C or C'. These are in turn alternatively moved up into the path 198, arrows 470, 472, or down, depending on which type of element is desired. The cartridge in turn is selected by rotating the holding rings (not shown in FIG. 14) about incubator 500 and stationary surface 510.

Referring again to FIG. 8A, it is desirable that the atmospheres for rings 30 and 32 be controlled, and further, that they be controlled separately. For example, relative humidity can be controlled by any mechanism. For most of station 20, this is easily done by wall 28' being a complete barrier between the two paths 22 and 24. However, as described and claimed in commonly-owned U.S. application Ser. No. 500,815 filed on Mar. 28, 1990 entitled "Analyzer Having Humidity Control Apparatus", to keep the atmospheres different, inter-mixing of atmospheres needs to be prevented when each path necessarily intersects the blade path 198. Thus, it is desirable that a seal be maintained at the top, in conjunction with the blade passage, to ensure that there is minimal air mixing between the two paths 22 and 24. A preferred embodiment to achieve these results is as follows:

The top portion 201 of the housing accommodates the passage of blade 414 and a test element dealt off the top of a stack from ring 30 or 32. More specifically, top portion 201 has a blade entrance port 202 and an exit port 204 fixed in the housing, and floating members 210, 212. The floating members are displacably seated on annular valve seats 214 disposed around an opening 216 that will allow a cartridge to be raised up into the path 198 to be engaged at groove 217 by blade 414. Members 210 and 212 are each biased downwardly against seats 214 by an expansion spring 218. Because each member 210 or 212 serves as a substitute blade guide if its cartridge is not raised up, a groove 220 horizontally extends through the member. Because each member is pushed up out of blade path 198 if its cartridge is raised up, a space 228 is formed in portion 200 to accommodate member 210 or 212 when spring 218 is compressed. (Movement upward of a stack elements E by rod 234 also causes cartridge C to be raised up against member 210 and 212.)

Although not essential, member 210 or 212 can be constructed so that top portion 230 thereof, from which boss 231 extends to receive spring 218, can be easily removed from bottom portion 232 (not shown), whereby any test element jams can be readily fixed.

Figure 8B:
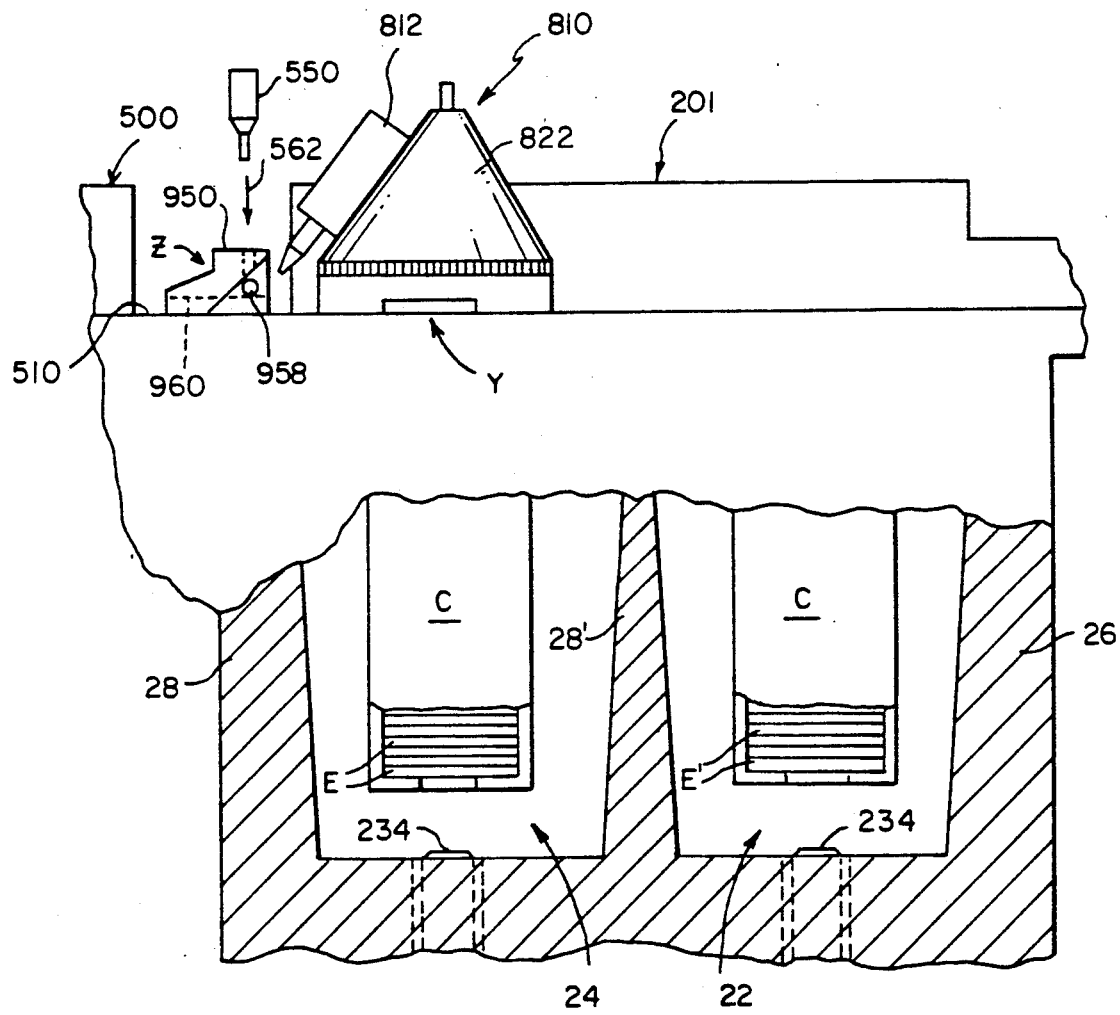
FIG. 8B is similar to FIG. 8A, except it shows the dispensing mechanism of FIG. 18 in place.
Figure 9:
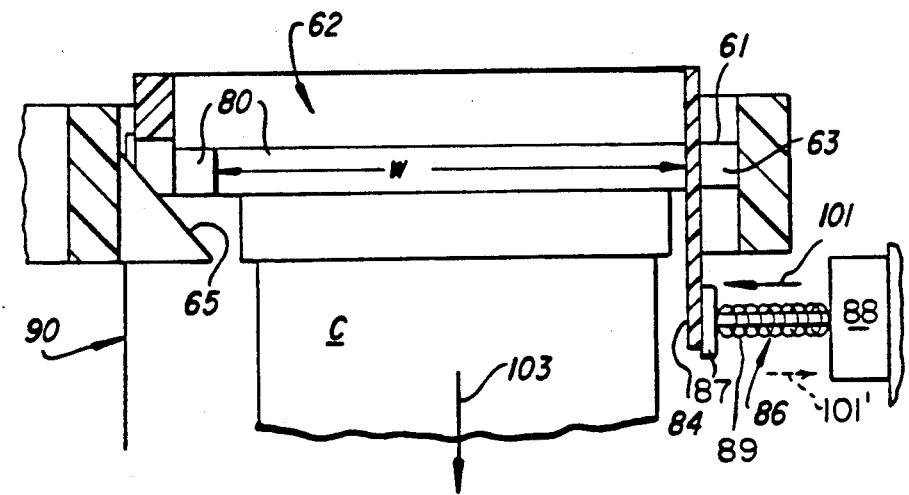
FIG. 9 is a fragmentary elevational view in section similar to FIG. 8A, but illustrating the parts in the cartridge-release position.

Elements E or E' are transferred by device 400 to support surface 510, FIGS. 1 and 8, where a dispensing probe 550, FIG. 8B, is used to dispense a patient sample onto the test element so transferred. Any such probe 550 can be used, including those automated probes conventionally used on analyzers available under the trademark "Ektachem E-700" Analyzer from Eastman Kodak Company.

The manner in which the sample is obtained by the sample-dispensing probe is not critical to this invention. The sample dispensing probe preferably includes pressurizing means, not shown, which can be integral with the rest of the analyzer described herein, or it can be provided by a separate stand-alone sample supply station that is coordinated to act in conjunction with this analyzer. For example, the sample-dispensing means and the mechanisms for loading it, described in commonly-owned U.S. Ser. No. 236,588 filed by James Shaw on Aug. 25, 1988 and entitled "Analyzers Using Linear Sample Trays with Random Access" can be used. In any event, any convenient apparatus for moving the probe from the sample location exterior of analyzer 20, to station A, arrow 560, FIG. 1, can be used.

A dispenser (not shown) similar to 550 is used to dispense reference liquid onto a PM element, at the same location at station A as is used by probe 550. Such reference liquid dispenser is preferably conventional.

The probe first moves horizontally, arrow 560, FIG. 1, from another portion of the analyzer handling patient samples, not shown, or from a different apparatus that supplies such samples to position "A". The probe then moves downward, arrow 562, FIG. 8, to be in position to dispense the sample.

Thereafter, blade 414 from device 400 pushes the test element further, arrow 570, into incubator 500, FIG. 1.

Turning next to incubator 500, it is preferably a rotating incubator with stations around its circumference each for holding a test element. Any such incubator can be used, there being a variety that are known in the art. Most preferably, it comprises, FIG. 15, an incubator of the type described in commonly-owned U.S. Ser. No. 346,205 filed on May 2, 1989 entitled "Universal Evaporation Cover", now U.S. Pat. No. 4,963,333. More specifically, incubator 500 preferably has a rotor 604 journaled at 612 on a shaft 614. Appropriate heating elements, not shown, are dispersed throughout incubator 500. Of the plurality of stations formed in the rotor, station A' is depicted. A spring 620 is captured at the station and is biased to press down on a cover 640 with a force F. Such a spring comprises a cover—engaging leg 621, a bias leg 622, and a vertical leg 624, leg 622 being captured behind a ridge 628 or rotor 604. A boss 650 can be mounted on the top of cover 640 to releasably engage an aperture 652 in leg 621. Vertical leg 624 rests on a support plate 662 that is apertured at 664 for the reading of colorimetric or rate-type test elements. Plate 662 is also the support of the test elements E and E', at the other stations. The undersurface of plate 662 is caused to ride over three spaced-apart buttons 670, in stationary surface 672, apertured at 666. The buttons are positioned to carefully control the height of the test element vis-a-vis a reflectometer 680, positioned to read a test element through apertures 664 and 666. Sensor 682 and flag 684 can be used to accurately sense when the stations are in their correct positions, e.g., for reading. As is conventional, reflectometer 680 preferably comprises a light source 686 and a detecting station 688 that senses the reflected light, arrow 690, from element E'.

In order for single incubator 500 to be acceptable for all three kinds of test elements (CM, rate and PM), incubator 500 is preferably modified in several ways to accommodate all three. For example, read station, so that the reflectometer is mounted to read rate and CM test elements while still on the incubator. Because each station at the incubator may have any one of the three types of test elements present, portions such as the evaporation cover at each station are modified so as to be effective regardless of the type of test element present.

Because some CM elements may involve end-point chemistries sensitive to light, preferably a chopper (not shown) is disposed between light source 686 and each aperture 666 to allow the light beam to strike a CM type element at any station only when it is at endpoint.

Figure 15:
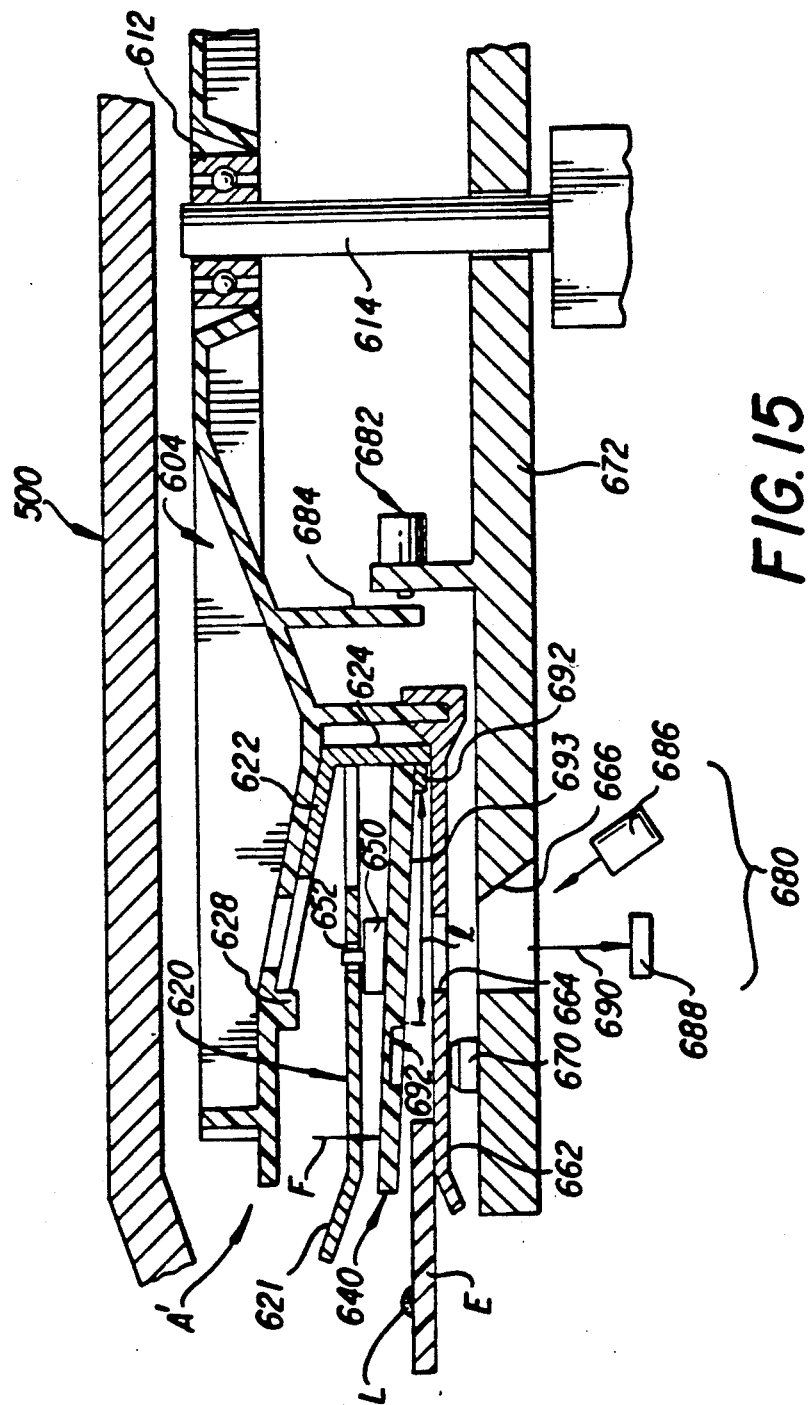
FIG. 15 is a fragmentary elevational view in section of an incubator useful in this invention.

Regarding evaporation cover 640, FIG. 15, this cover is preferably grooved at 692 to provide clearance for liquid drops L on a PM type test element (element E that is shown), while at the same time providing for a sufficient length "l" to rear edge 692 that will ensure that non-grooved surface portion 693 seals over the liquid-bearing portion of a CM or rate-type test element, as is described and claimed in the aforesaid commonly-owned U.S. application Ser. No. 346,205 filed on May 2, 1989, entitled "Universal Evaporation Cover". (Because no liquid protrudes from such a CM or rate-type element, no clearance groove is needed). Most preferably, surface portion 693 and indeed all of cover 640 is manufactured from a non-porous material such as polyethylene.

Figure 17:
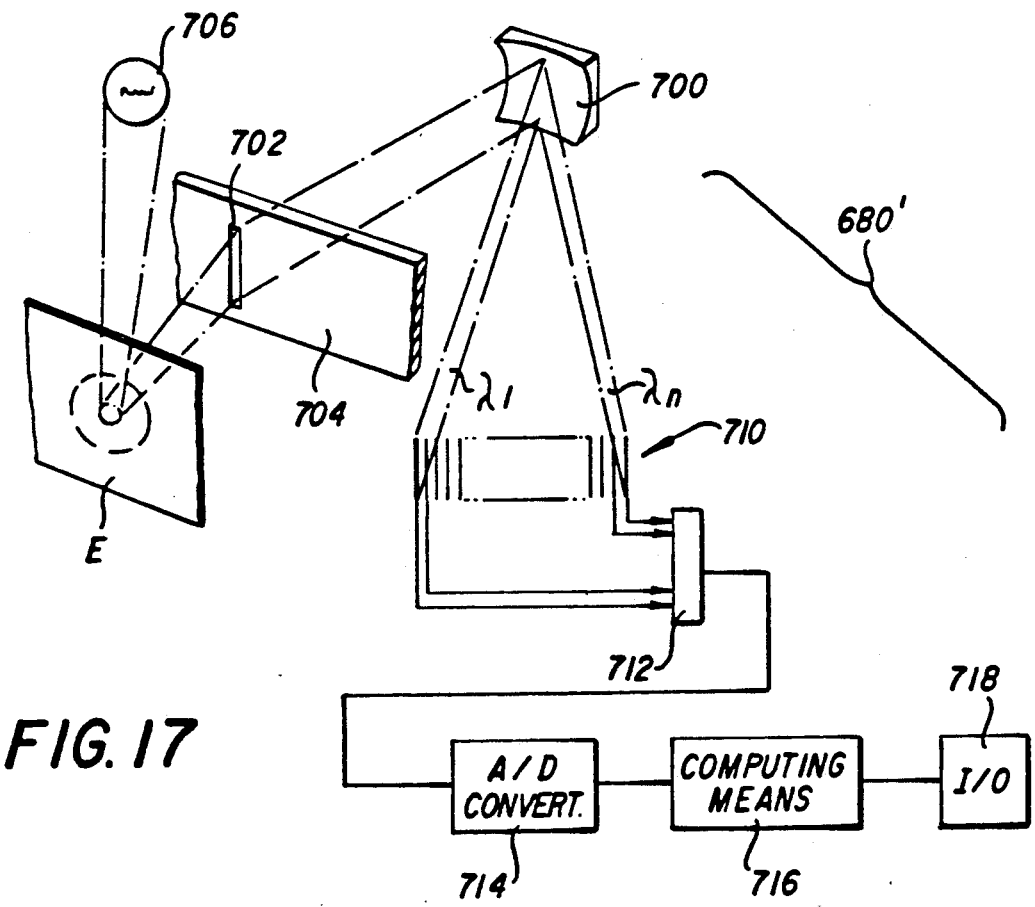
FIG. 17 is a schematic illustration of a preferred reflectometer useful in the invention.

Any suitable reflectometer 680 can be used. Highly useful is a diffraction grating reflectometer 680′, FIG. 17. Such a reflectometer features a conventional holographic diffraction grating 700, that uses a slit 702 in mask 704 to direct a line exposure of the light reflected from element E from the light source 706. (Fiber optics, not shown, can be used to carry the light images.) Grating 700 in turn breaks the image into a continuous spectrum of wavelengths $\lambda_i = \lambda_l$ through $\lambda_n$, which fall as a linear array on an image plane 710. A suitable array of imaging detectors 712 is used to detect the array of wavelengths, wherein each element of the detector 712 detects only one of the wavelengths $\lambda_i$, and the entire image within the wavelength. The signal from detector 712 is processed by an A/D converter 714 and sent via computing means 716 to a suitable I/O unit 718, such as a CRT display. Further details on diffraction grating reflectometers can be found in U.S. Pat. No. 4,544,271.

Not all test elements are read by reflectometer 680. Specifically, PM type test elements require an electrometer 360, FIGS. 1 and 2. Such an electrometer is conventional, and uses two electrical probes, not shown, that are pushed down into contact with a PM test element moved out of the incubator, arrow 362, onto support surface 510, by a conventional pusher blade 363, FIG. 2.

After a PM test element is read, it is moved to an aperture 364 in support surface 510, where it falls out of the analyzer. A similar dump aperture 366 is provided for spent CM or rate test elements. Those are pushed from the incubator, arrow 368, to aperture 366 by a conventional pusher blade 369.

Figure 16:
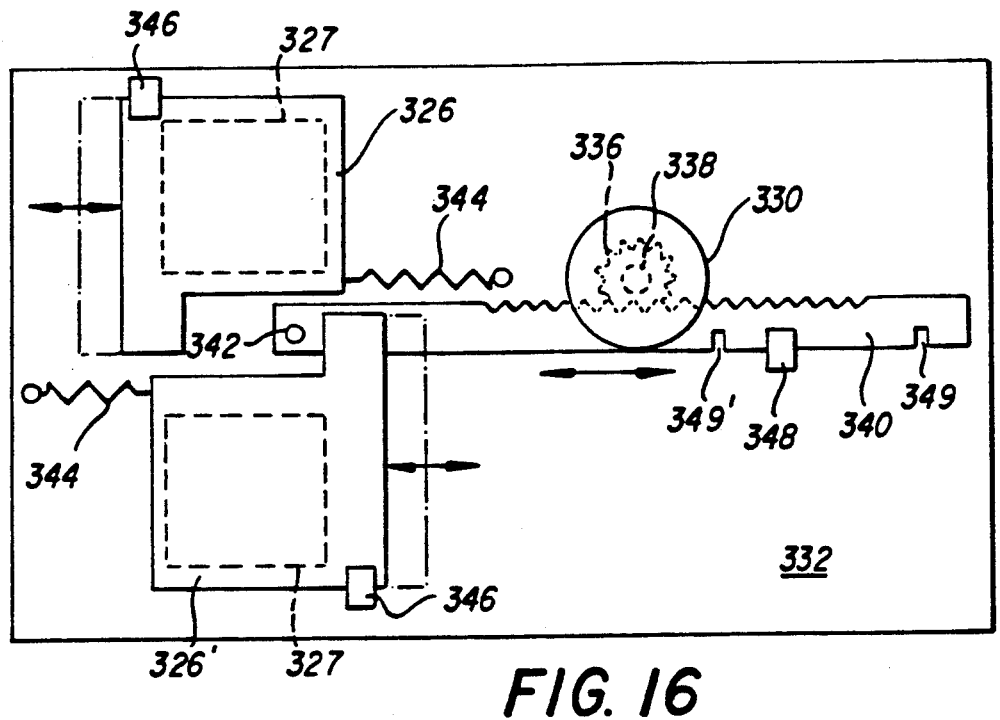
FIG. 16 is a fragmentary plan view looking up, of a mechanism for unloading cartridges from the mounting means shown in FIG. 8, using the doors partially shown in FIG. 10.

The final station of analyzer 20 to be encountered by a cartridge, during its residence in the analyzer, is the discharge portion of station 300, FIGS. 13 and 16. This portion features a door 326, 326′ for each of the two paths 22 and 24, as is especially shown in FIG. 16. Each such door opens and closes aperture 327, and is independently operable by a motor 330, FIG. 13. Alternatively, they could be operated together even though it is unlikely both would be needed to discharge a spent cartridge at the same time.

A useful construction of doors 326 and 326′, FIG. 16, includes the following: Floor member 332 of housing 302 hangs a motor 330 from its undersurface, FIG. 13, that operates a pinion gear 336 off its drive shaft 338, FIG. 16. Gear 336 in turn operates a rack 340 that has a post 342 at one end. Post 342 bears on a portion of door 326 or 326′, alternatively, to push such door to operate against tension spring 344 that biases its respective door closed. Sensors 346 sense the position of door 326 or 326′, and sensor 348 senses a flag 349 or 349′ in rack 340. In this fashion, a single motor can independently operate two independent doors for the discharge of cartridges.

Figure 18:
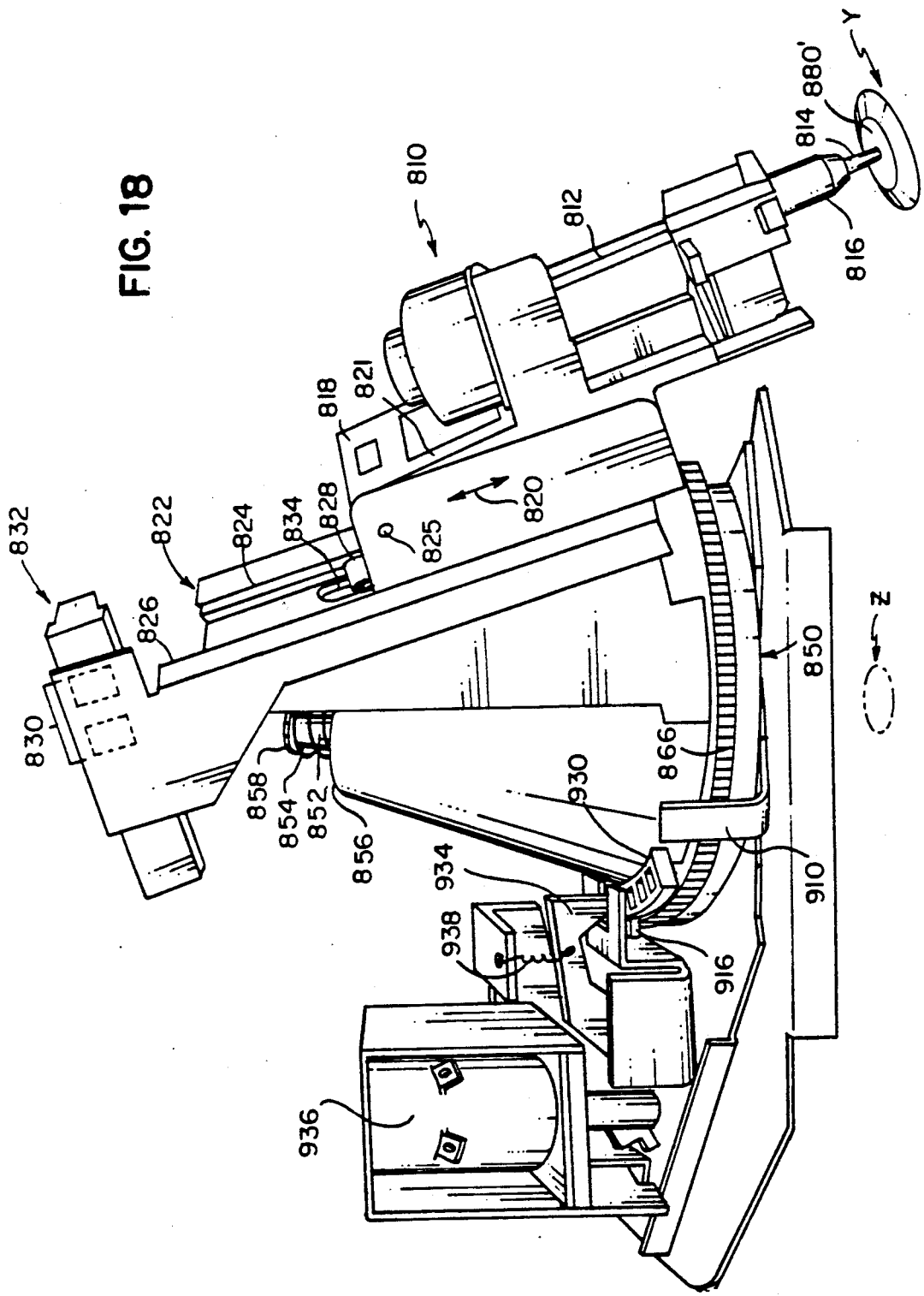
FIG. 18 is a perspective view of a liquid-aspirating and dispensing mechanism useful in the analyzer.

FIG. 18 provides details of the reference liquid dispensing mechanism 810 illustrated in FIGS. 2 and 8B. Such mechanism comprises a pump 812, a tip support 816 holding a tip 814, a pump carrier 822 for moving pump and tip vertically and rotationally between two operative positions Y and Z, a cam 850 cooperating with the carrier 822 to achieve this movement, a cam follower 836, FIG. 22, connecting carrier 822 with cam 850, and rotating means 866, 868 and 870 to rotate cam 850.

Most preferably, mechanism 810 is improved as follows:

Pump 812, of conventional construction, includes a housing 818 to which pump 812 is connected. Preferably, housing 818 of pump 812 comprises, FIG. 21, a body 819 that has a yoke 821 extending therefrom to two lugs 823 that pivot to frame 818 at 825. Housing 818 reciprocates, arrow 820, FIG. 18, on a carrier 822 having opposite rails 824, 826 between which housing 818 slides. A position-sensor flag 828 is mounted on the top of housing 818 to cooperate with sensing means 830 located at the top 832 of carrier 822. See also FIG. 21.

Carrier 822, FIG. 18, is shaped to slip over a cam mechanism 850 that carrier 822 frictionally engages. A slot 834 is formed in carrier 822 between rails 824, 826 to allow a cam follower 836, FIG. 22, and its idler arm 838, to project through. Arm 838 is fixed to pump 812 or its housing 818. Preferably, a shoulder 840 projects from pump 812 or its housing to also guide the pump within slot 834.

Figure 19:
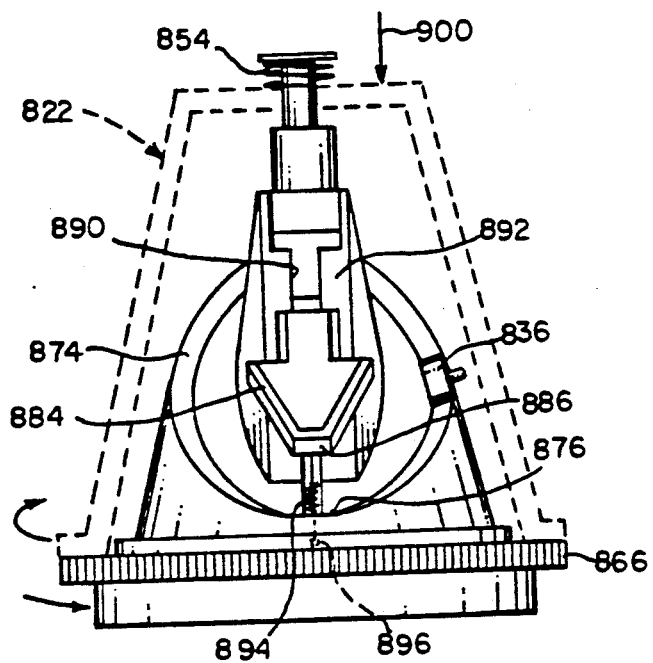
FIG. 19 is a fragmentary elevational view of the cam of the assembled mechanism of FIG. 18, showing the cam follower at a raised position at which the pump dispenser is inoperative.
Figure 22:
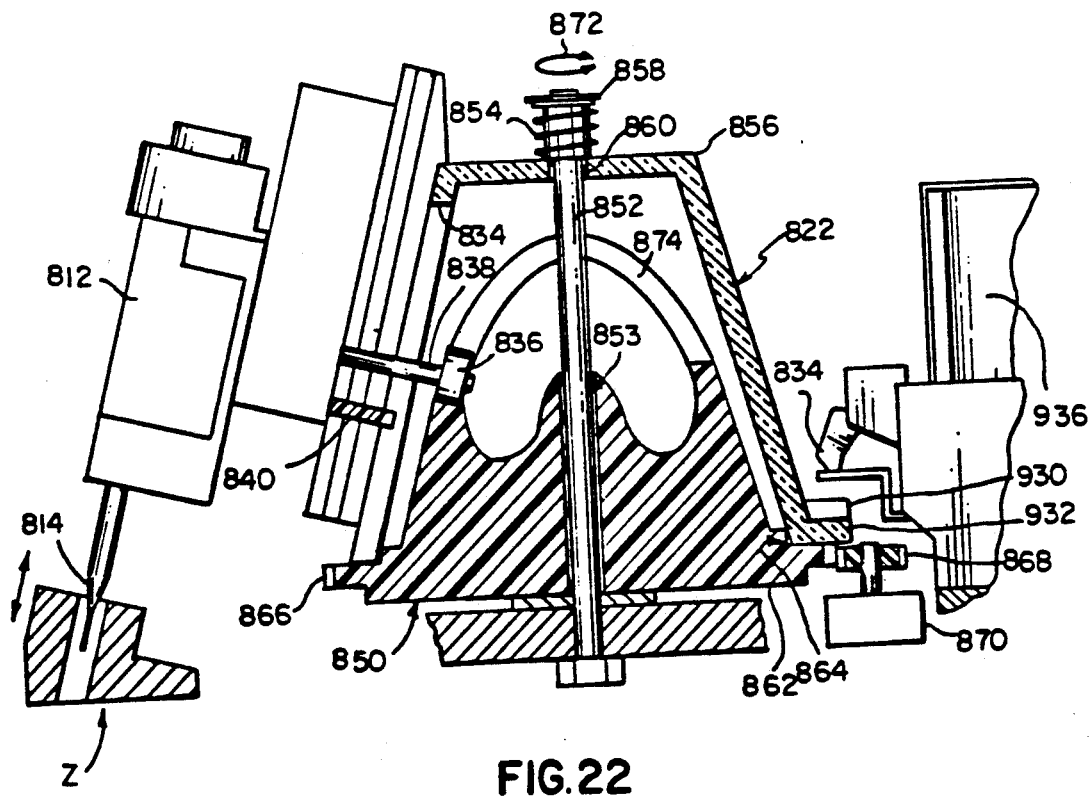
FIG. 22 is a section view taken generally along the line 22—22 of FIG. 20, to show the pump mounting on its carrier.
Figure 23A:
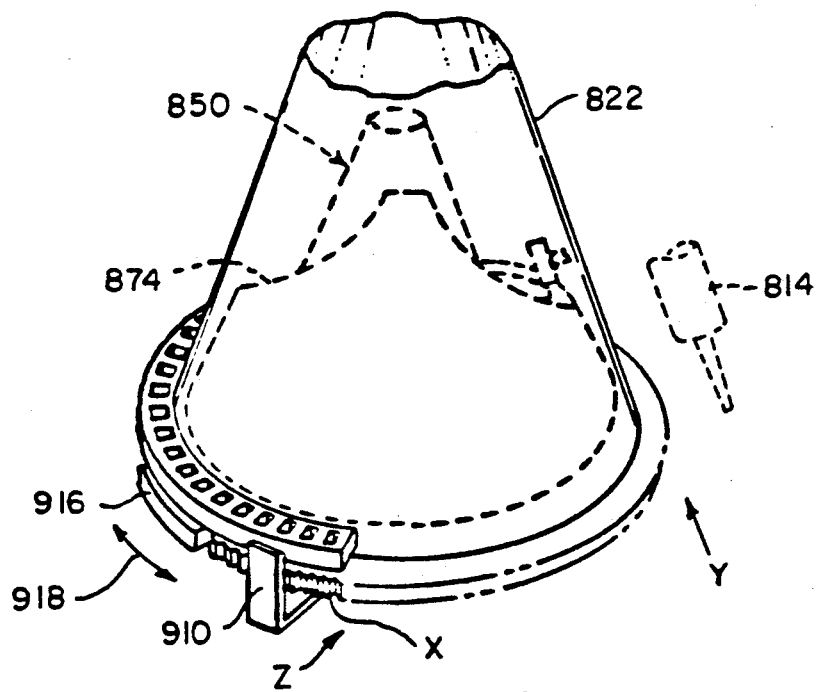
FIG. 23A and 23B are fragmentary perspective views of the pump carrier and the cam (shown in phantom) to illustrate the relative movement between the two.
Figure 23B:
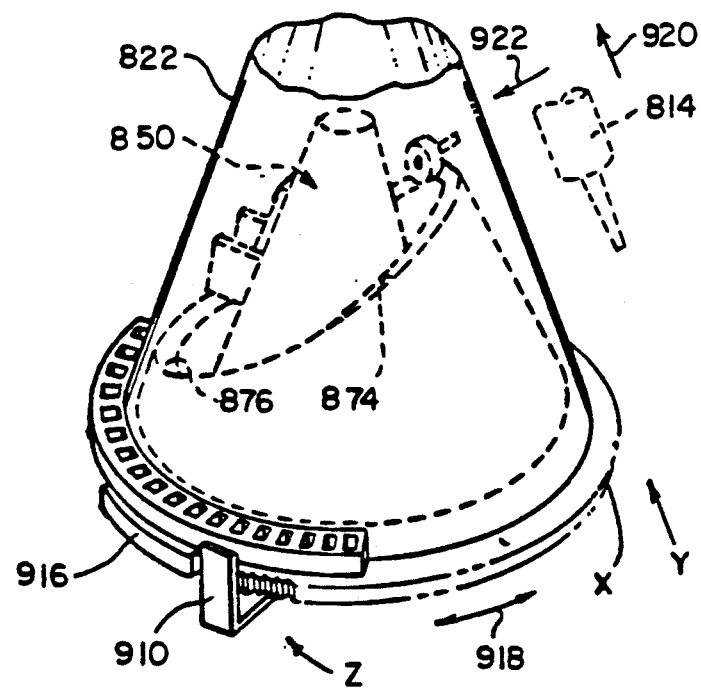

The frictional engagement of cam 850 by carrier 822 is preferably achieved, FIGS. 19 and 22, by a central fixed post 852 that passes through center portion 853 of the cam, FIG. 22, a compression spring 854 surrounding the post and bearing on end wall 856 of carrier 822, and a retaining clip 858. End wall 856 is apertured at 860, FIG. 22, to accommodate post 852 that projects therethrough.

Bottom wall 862 of cam 822 adjoins a curved sidewall 864 that is preferably provided with gear teeth 866. Most preferably, sidewall 864 at the teeth portion 866 is circular. Gear teeth 866 are positioned and shaped to engage a pinion gear 868 driven by a conventional motor 870, to cause cam 822 to rotate about the axis of post 852, arrow 872.

A critical aspect of cam 822 is cam track 874, extending in three dimensions around post 852, as shown in FIGS. 19, 21, 22 and 23A-23B. Track 874 includes a bottom-most portion 876, FIGS. 21 and 23B, and all the rest of the track that rises above that portion to completely encircle post 852, FIG. 22. Because cam 850 is preferably conical in overall shape as shown in this embodiment, track 874 also traces the surface of the cone defined by this portion of cam 850. The uppermost portion 878 of track 874 is generally opposite to the lowermost portion 876, that is, on the opposite side of post 852, as best shown in FIG. 21.

Cam follower 836 rides on track 874 due to gravity, except when pump carrier 822 and its cam follower are at bottom portion 876. At this time, the pump is at one of the two operative stations Y or Z, station Z being schematically shown in FIG. 18 and partially schematically in FIG. 21. At either station, a top surface 880 or 880′ is effective to resist further downward advance of tip 814 or pump 812. As a result, cam follower 836 is lifted off of track 874. However, to be sure that tip 814 is in fact completely seated at the station (for dispensing or aspirating, as the case may be), means are provided for biasing the cam follower downward with a predetermined positive force F, arrow 882, FIG. 21. Such means preferably comprise a downwardly-directed camming surface 884, preferably V-shaped with the bottom-most portion 886 representing the complete sealing position of cam follower 836, and hence of tip 814 at either station Y or Z. See especially FIG. 19.

To bias camming surface 884 downwardly, that surface is slidably mounted in a track 890 on face 892 of cam 850. Inside track 890, a tension spring 894 is connected at one end to surface 884, and at its opposite end 896 to cam 850.

Figure 20:
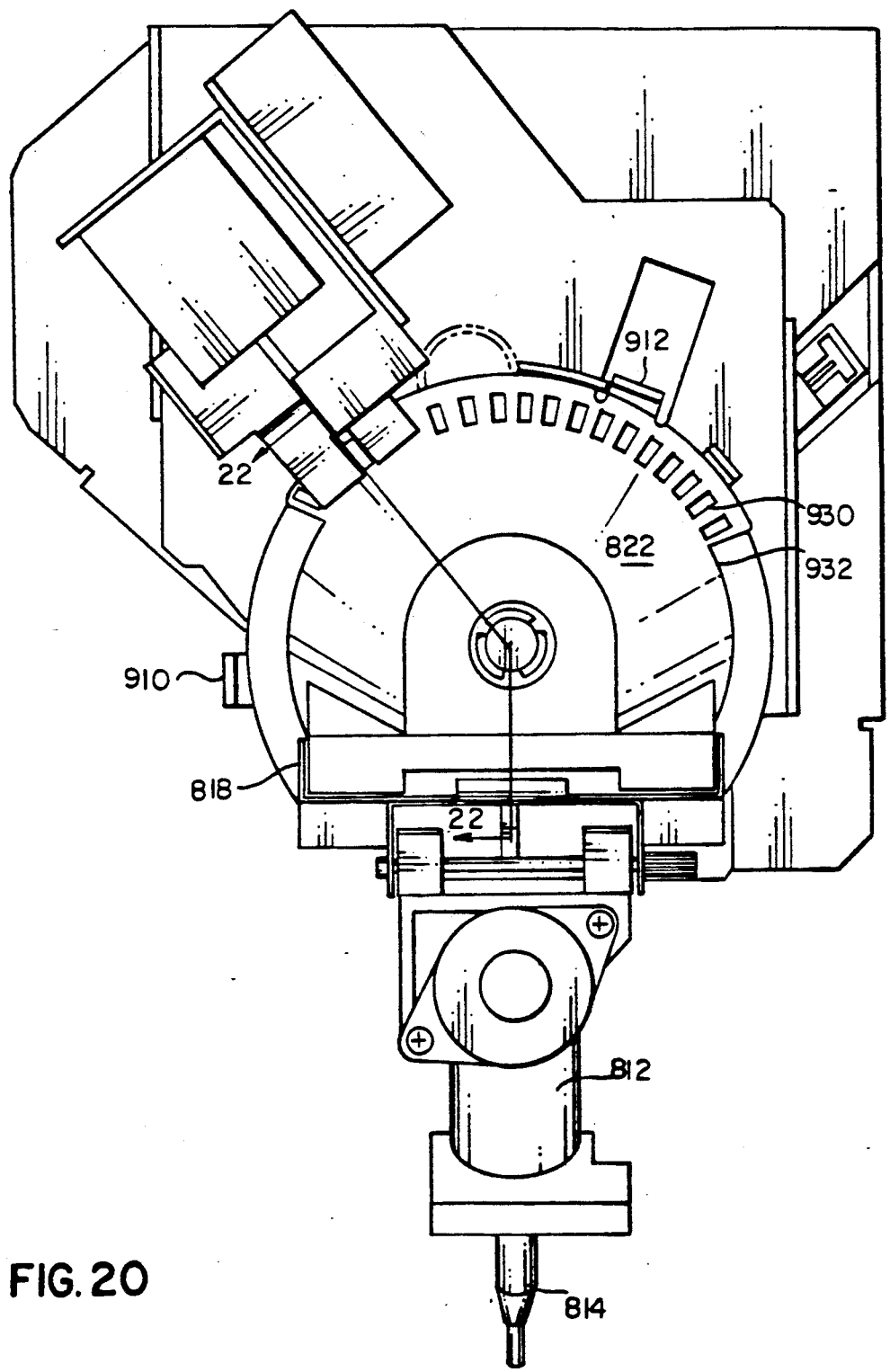
FIG. 20 is a plan view of the mechanism of FIG. 18.

Because of the downward force F, arrow 900 (FIG. 19), exerted by spring 854, pump carrier 822 generally rotates with cam 850 as it is driven to rotate. However, means are provided, such as two limit members 910 and 912 fixed to support 914 of mechanism 810, FIGS. 18 and 20, to stop rotation of carrier 822 and to confine its rotation within the arc between members 910 and 912. An outwardly projecting lip 916 is formed integral with carrier 822, FIG. 18 and especially FIGS. 23A and 23B. Lip 916 is sized and positioned to abut against either limit member 910 or 912 as cam 850 rotates, arrow 918, FIGS. 23A and 23B. The effect, of course, is to cause carrier 822 to come to a stop at a limit member, e.g., member 910, FIG. 23B, while cam 850 continues to rotate inside carrier 822. That is, gear tooth X, FIG. 23A, continues to rotate to its position shown in FIG. 23B, even though carrier 822 does not progress beyond the position shown in FIG. 23B. This in turn causes cam track 874 (in phantom) to continue to rotate relative to the now stationary carrier 822, as is shown by the relative positional changes of track 874 in FIG. 23B from that of FIG. 23A. Cam follower 836 in turn is forced, along with the pump and tip 814, to rise up since track 874 is "rising", arrow 921, FIG. 23B. In the raised "inoperative" position shown in FIG. 23B, (in phantom), the pump and tip 814 are in position to be rotated (arrow 922) from that station (station Y) to station Z, without bumping into structure that is otherwise in the way. This is achieved by reversing the rotation of cam 850, arrow 924, at which time carrier 822 again moves with cam 850 until the other limit member (912, not shown in FIG. 23B) encounters lip 916 to force carrier 822 to once again stop while cam 850 continues in the direction of arrow 924.

Because the same reference liquid is aspirated from station Y for many tests, tip 814 need not be replaced frequently. However, it is replaced for maintenance and cleanliness on occasion, e.g., once every day, and for this purpose, means are included for removably locking carrier 822 to its last known position while tip 814 is manually removed. Such locking means preferably comprise, FIGS. 18 and 22, teeth 930 molded into side edge 932 of carrier 822, adjacent lip 916. Cooperating with teeth 930 is a lock lever 934 actuated by a solenoid 936 to be either in a raised position, as shown, or a lowered position to engage teeth 930 to lock against relative rotation of carrier 822. Optionally, a tension spring 938, FIG. 18, can be used to bias lever 934 upward into its disengaged position, so that solenoid 936 need only lower lever 934. In use, lever 934 is effective to hold carrier 822 in place to allow maintenance of the pump and tip 814. For such maintenance, the pump 812 is preferably pivoted, arrow 940, upwardly about pivot 825, FIG. 21.

The operation of dispensing mechanism 810 and dispenser probe 550 will be readily apparent from the preceding description. That is, they both cooperate with a fixed dispensing block 950, FIGS. 2 and 8, having a turret 952 with twin dispense holes 954, 956, FIG. 2, and a side aperture 958. The holes 954 and 956 are used by probe 550, FIG. 8—hole 954 if the test element to be spotted is an ISE type element, and hole 956 if it is a colorimetric type element. (The test element slides into block 950 at a horizontal groove 960, FIG. 8B). Tip 814 enters side aperture 958 for dispensing only if the test element is an ISE type element. The engagement of aperture 958 is also shown in FIG. 21.

The invention has been described in detail with particular reference to certain preferred embodiments thereof, but it will be understood that variations and modifications can be effected within the spirit and scope of the invention.

What is claimed is:

1. In an analyzer for assaying for analytes of a body liquid on dried test elements, said analyzer comprising
   means for temporarily storing a plurality of stacks of dried test elements, the test elements in any one stack being for the same assay while each stack is generally for a different assay selected from any one of three different types selected from potentiometric, colorimetric or rate-type test elements,
   an incubator for test elements taken from a stack,
   and means for detecting a change in a test element after incubation in said incubator;
   the improvement wherein, to move said stacks of elements, said analyzer further comprises means defining at least one generally circular, horizontal path generally centered on said incubator,
   first moving means for moving said stack-storing means around said at least one path,
   means for temporarily holding a stack on said first moving means, said holding means being capable of at least two alternate states, one which holds a stack on said path and the other which releases a stack from said path,
   means for alternating said holding means between said two states,
   and means for transferring a test element to said incubator from any stack held on said path,
   and wherein said incubator is constructed to receive all the types of said test element,
   whereby said incubator can be used to incubate all three types of test elements.

2. In an analyzer for assaying for analytes of a body liquid on dried test elements, said analyzer comprising
   means for temporarily storing a plurality of stacks of dried test elements, the test elements in any one stack being for the same assay while each stack is generally for a different assay selected from any one of three different types selected from potentiometric, colorimetric or rate-type test elements,
   an incubator for test elements taken from a stack,
   and means for detecting a change in a test element after incubation in said incubator;
   the improvement wherein, to move said stacks of elements, said analyzer further comprises means defining at least one generally circular, horizontal path generally centered on said incubator,
   first moving means for moving said stack-storing means around said path,
   means for temporarily holding a stack on said moving means, said holding means comprising a member mounted on said moving means to move between a first position that holds a cartridge for said stack and a second position that releases a cartridge, second moving means for moving said holding member between said first and second positions, and means for transferring a test element from any stack held on said path to said incubator, and wherein said incubator is constructed to receive all three types of said test elements, whereby said incubator can be used to incubate all three types of test elements.

3. An analyzer as defined in claim 2, wherein said second moving means comprise means for biasing said holding member into said first position, and means for overriding said biasing means to move said holding member to said second position to release a cartridge.

4. In an analyzer for assaying for analytes of a body liquid on dried test elements, said analyzer comprising means for temporarily storing a plurality of stacks of dried test elements, the test elements in any one stack being for the same assay while each stack is generally for a different assay selected from any one of potentiometric, colorimetric or rate-type test elements, an incubator for test elements taken from a stack, and means for detecting a change in a test element after incubation in said incubator;

the improvement wherein said analyzer further comprises means defining at least one generally circular, horizontal path generally centered on said incubator, first moving means for moving said stack-storing means around said path, means for temporarily holding a stack on said moving means, said holding means comprising a member mounted on said moving means to move between a first position that holds a cartridge for said stack and a second position that releases a cartridge, a second moving means for moving said holding member between said first and second positions, said second moving means comprising means for biasing said holding member into said first position, and means for overriding said biasing means to move said holding member to said second position to release a cartridge, and means for transferring a test element from any stack held on said path to said incubator, whereby said incubator can be used to incubate all three types of test elements, and further comprising means defining a second generally circular horizontal path centered on said incubator and spaced from said at least one path, and means for moving said stack-storing means around said second path, said moving means of said second path being independent from said first moving means of said at least one path.

5. An analyzer as defined in claim 4, wherein each of said paths comprises a ring having a surface for supporting a stack-containing cartridge and cut-out portions in said surface each of which is sufficient in size to accommodate a cartridge, and wherein said holding member comprises a frame including a cartridge-support shoulder disposed at the same level as said ring support surface, and means for slidably mounting said frame on said ring support surface and partially within said cut-out so as to move between said first position and said second position.

6. An analyzer as defined in claim 5, and further comprising discharge means associated with each of said paths for discharging from said paths a cartridge previously containing a stack, when the cartridge is released by said overriding means.

7. An analyzer as defined in claim 6, wherein said discharge means comprise a door and an exit port, and door-moving means for slidably moving said door to cover or uncover said exit port.

8. An analyzer as defined in claim 7, wherein said door-moving means comprise a single motor connected to actuate independently said door for each of said paths.

9. An analyzer as defined in claim 1 or 2, wherein said path comprises a ring having a surface for supporting a stack-containing cartridge and cut-out portions in said surface each of which is sufficient in size to accommodate a cartridge, and wherein said holding means comprise a frame comprising a cartridge-support shoulder disposed at the same level as said ring support surface, and means for slidably mounting said frame on said ring support surface and partially within said cut-out so as to move between said first position and said second position.

10. An analyzer as defined in claim 1 or 2, and further comprising discharging means associated with said path for discharging from said path a cartridge previously containing a stack.

11. An analyzer as defined in claim 10, wherein said discharge means comprise a door and an exit port, and door-moving means for slidably moving said door to cover or uncover said exit port.

12. In an analyzer for assaying for analytes of a body liquid on dried test elements, said analyzer comprising means for temporarily storing a plurality of stacks of dried test elements, the test elements in any one stack being for the same assay while each stack is generally for a different assay selected from any one of potentiometric, colorimetric or rate-type test elements, an incubator for test elements taken from a stack, and means for detecting a change in a test element after incubation in said incubator;

the improvement wherein said storing means further comprises means for temporarily holding a stack of elements in a cartridge, said holding means being configured to fit generally around a stack of said elements, means for moving said holding means along a generally circular path around a center, and means for slidably moving said holding means between two positions on a radius of said circular path, one of said positions being one which allows a cartridge to fall, and the other said positions being one which holds up a cartridge.

13. An analyzer as defined in claim 12, wherein said holding means comprise a frame member comprising first means fitting under a cartridge to support it, and said moving means comprises second means opposite to said first means and fitting under a cartridge for supporting it, said frame member being movable on said moving means, said slidable moving means being effective to move said first and second means apart in said one position and close together in said other position, said first and second means being far enough apart in said one position to cause a cartridge to fall between them.

14. An analyzer as defined in claim 13, wherein said slidable moving means comprise biasing means for biasing said frame member with said first and second supporting means in said other position, and overcoming means for overcoming said biasing means to move said first and second supporting means into said one position.

15. An analyzer as defined in claim 13 or 14, wherein said member moving-means comprise a generally flat annular ring having a plurality of spaced-apart cut-out portions therein each having a size and shape to accommodate a cartridge, a portion of said ring at one edge of said cut-out shape being provided with a first pair of inwardly projecting shoulders, and a motor operable to rotate said ring around said circular path.

16. An analyzer as defined in claim 14, wherein said overcoming means comprise a push member, a spring to hold said push member away from said frame member, and a solenoid constructed to push said push member against said frame member and contrary to the action of said spring.

17. An analyzer as defined in claim 1, 2 or 12, and further comprising means for depositing a patient liquid onto a test element removed by said transfer means from said storing means, said depositing means being positionable adjacent to said incubator and said transferring means.

18. An analyzer as defined in claim 1, 2 or 12 and further comprising a liquid dispensing mechanism for dispensing a standard liquid comprising a pump, a tip support on said pump for holding a liquid-containing tip, means for moving said pump and a tip on said support vertically and rotationally between at least two operative positions in which liquid is either aspirated into a tip or dispensed from a tip, and inoperative positions above and between said operative positions, said moving means including a rotatable three-dimensional cam, a cam follower mounted to move on said cam, and means for rotating said cam about a vertical axis between said at least two operative positions in response to command signals.

19. An analyzer as defined in claim 18, wherein said moving means further comprises a carrier mounted over and surrounding said cam, said pump being slidably mounted for reciprocation on said carrier and attached to said cam follower, said carrier having a slot therein constructed to permit passage through said carrier of said pump cam follower to said cam, said slot extending in a direction that falls in a plane through said axis of rotation, means for frictionally coupling said carrier to said cam to rotate with said cam, and means for limiting the rotation of said carrier, but not said cam, between two circumferential positions on said cam that correspond to said at least two operative positions, to force said cam follower to move relative to said cam.

20. An analyzer as defined in claim 18, wherein said cam comprises a downwardly extending track portion which extends below the lowest point of travel of which said pump cam follower is capable of traveling, and further comprising means for biasing said cam follower downward with a positive force when said cam follower is located at its lowest point of travel so that a tip on said pump can be sealed by said positive force in a housing when it is in its downward, at least two operative positions.

21. An analyzer as defined in claim 18, and further comprising on said carrier, means for removably locking said carrier in any position between or at said at least two operative positions, so that maintenance can be performed on said pump without disturbing the last-known location of said carrier.

22. An analyzer as defined in claim 1, 2, or 12, wherein said incubator is the only incubator present in the analyzer for receiving and holding simultaneously a plurality of test elements.

23. Apparatus for temporarily supporting a stack of planar, slide-like elements in a predetermined vertical position, said apparatus comprising means defining at least one generally circular, horizontal path and first moving means for moving a stack of elements around said at least one path, means for temporarily holding a stack on said moving means, said holding means comprising a member mounted on said moving means to move between a first position that holds a cartridge for said stack and a second position that releases a cartridge, and second moving means for moving said holding member between said first and second positions, wherein said stack-moving means and said holding member each comprise a pair of stack-supporting shoulders, each pair being mounted opposite to the other to cooperate to hold up a stack of test elements.

24. Apparatus as defined in claim 23, wherein said second moving means comprise means for biasing said holding member into said first position, and further comprising overriding means for overriding said biasing means to move said holding member to said second position to release a cartridge.

25. Apparatus as defined in claim 24, wherein said overriding means comprise a push member, a spring to hold said push member away from said holding member, and a solenoid constructed to push said push member against said holding member and contrary to the action of said spring.

26. Apparatus for temporarily supporting a stack of planar, slide-like elements, in a cartridge held in a predetermined vertical direction, said apparatus comprising means for temporarily holding a cartridge of elements, means for moving said holding means along a generally circular path around a center, and means for slidably moving said holding means between two positions on a radius of said circular path, one of said positions being one which allows a cartridge to fall, and the other of said positions being one which holds up a cartridge.

27. Apparatus as defined in claim 26, wherein said cartridge-holding means comprise opposite shoulders configured to fit under a portion of a cartridge and said slidable moving means is constructed to move said shoulders together and apart.

28. Apparatus as defined in claim 27, wherein said slidable moving means comprise biasing means for biasing said opposite shoulders together to occupy said other position, and means for overcoming said biasing means to move said opposite shoulders apart into said one position.

29. Apparatus as defined in claim 27 or 28, wherein said moving means comprise a generally flat annular ring having a plurality of spaced-apart cut-out portions therein each having a size and shape to accommodate a cartridge, a portion of said ring at one edge of said cut-out shape being provided with a pair of inwardly projecting shoulders, and a motor operable to rotate said ring around said circular path, and said holding means comprise a frame on said ring with a second pair of shoulders projecting towards said first pair.

30. Apparatus for temporarily supporting a stack of planar, slide-like elements, said apparatus comprising a flat generally annular ring having a plurality of spaced-apart cut-out portions therein each having a size and shape to accommodate a cartridge containing a stack of said elements, a portion of said ring at one edge of said cut-out shape being provided with a first pair of inwardly projecting shoulders, a nesting frame member constructed to slidably fit in each of said cut-out portions, said frame member being apertured to receive a cartridge therein, a first portion of said frame member being adopted to slidably rest on said ring with said inwardly projecting shoulders being insertable into said aperture of said frame member, and a second portion of said frame member being provided with a second pair of inwardly projecting shoulders positioned to be at about the same level as said first pair when said frame member is on said ring;

and biasing means mounted on said frame member adjacent said second pair of shoulders for temporarily urging said frame member along said support so that said first pair of shoulders is inserted into said frame aperture, whereby both pairs of shoulders cooperate to hold up a cartridge.

31. Apparatus as defined in claim 30, and further comprising means for overriding said biasing means and for sliding said frame member on said support so that said first pair of shoulders no longer is inserted into said aperture.

32. A method for supplying a test element from any one of three different kinds to an incubator prior to the test elements being examined to detect a change, comprising the steps of supplying slide-like test elements selected from CM-type, rate-type, and PM-type, as a plurality of stacks wherein the test elements of each stack are identical within the stack, mounting said stacks on at least one generally circular path surrounding a central incubator, moving said stacks around said path until a selected stack reaches a predetermined position, and transferring a test element from said stack at said predetermined position to said incubator.

33. A method as defined in claim 32, wherein each stack is held in a cartridge, and further comprising the step of discarding a cartridge from said path when all the elements from the stack have been transferred.

34. A method as defined in claim 33, wherein said discarding step comprises the step of dropping the cartridge away from the path.

35. A method as defined in claim 32, wherein said transferring step comprises pushing a test element off one end of the stack into said incubator.

36. A method as defined in claim 32, wherein said transferring step comprises first transferring a test element to a position outside the incubator, dispensing a sample liquid onto the transferred test element at said outside position, and thereafter transferring the dispensed sample and test element from said outside position into said incubator.

37. A method as defined in claim 32, wherein said step of transferring of test elements comprises the step of transferring them only to said incubator as the means for incubating test elements prior to detection of a change in the test element.

* * * * *